United States Patent
Shibutani et al.

(10) Patent No.: US 8,329,739 B2
(45) Date of Patent: Dec. 11, 2012

(54) PHENYLIMIDAZOLE COMPOUNDS

(75) Inventors: Tadao Shibutani, Naruto (JP); Koushi Iwata, Naruto (JP); Satoshi Kido, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 13/145,041

(22) PCT Filed: Feb. 3, 2010

(86) PCT No.: PCT/JP2010/051469
§ 371 (c)(1),
(2), (4) Date: Jul. 18, 2011

(87) PCT Pub. No.: WO2010/090200
PCT Pub. Date: Aug. 12, 2010

(65) Prior Publication Data
US 2011/0275823 A1    Nov. 10, 2011

(30) Foreign Application Priority Data

Feb. 4, 2009 (JP) .................. 2009-023793
Nov. 9, 2009 (JP) .................. 2009-255980

(51) Int. Cl.
*A61K 31/4174* (2006.01)
*C07D 233/64* (2006.01)
(52) U.S. Cl. .................. 514/397; 548/311.1
(58) Field of Classification Search .................. 514/397; 548/311.1
See application file for complete search history.

(56) References Cited

U.S. PATENT DOCUMENTS 4,665,023 A    5/1987   Deneke et al.
2011/0065728 A1   3/2011   Neagu et al.

FOREIGN PATENT DOCUMENTS

| JP | 60-224677 A | 11/1985 |
|---|---|---|
| WO | 01/27088 A1 | 4/2001 |
| WO | 2008/153957 A1 | 12/2008 |
| WO | 2009/139076 A1 | 11/2009 |
| WO | WO-2009/139076 A1 * | 11/2009 |

OTHER PUBLICATIONS

Kazuhiko Tsutsumi, et al., "The Novel Compound NO-1886 Increases Lipoprotein Lipase Activity with Resulting Elevation of High Density Lipoprotein Cholesterol, and Long-term Administration Inhibits Atherogenesis in the Coronary Arteries of Rats with Experimental Atherosclerosis", J. Clin. Invest., vol. 92, pp. 411-417 (Jul. 1993).

Kazuhiko Tsutsumi, et al., "Suppression of Hyperlipidemia-Associated Cataracts in Diabetic Rats with the Lipoprotein Lipase Activator NO-1886", Biol. Pharm. Bull., vol. 19, No. 12, pp. 1570-1573 (1996).

Ikuo Kawamura, et al., "Effect of Lipoprotein Lipase Activators Bezafibrate and NO-1885, on B16 Melanoma-Induced Cachexia in Mice", Anticancer Research, vol. 19, pp. 4099-4104 (1999).

Kaori Nakayama, et al., "Effect of the Lipoprotein Lipase Activator NO-1866 on Adriamycin-Induced Nephrotic Syndrome in Rats", Metabolism, vol. 49, No. 5, pp. 588-593 (May 2000).

Kazuhiko Tsutsumi, et al., "Correction of Hypertriglyceridemia with Low High-Density Lipoprotein Cholesterol by the Novel Compound NO-1886, a Lipoprotein Lipase-Promoting Agent, in STZ-Induced Diabetic Rats", Diabetes, vol. 44, pp. 414-417 (Apr. 1995).

M. Kusunoki, et al., "The lipoprotein lipase activator, NO-1886, suppresses fat accumulation and insulin resistance in rats fed a high-fat diet", Diabetologia, vol. 43, pp. 875-880 (2000).

Supplementary European Search Report dated Aug. 16, 2012 in EP 10 73 8531.

* cited by examiner

*Primary Examiner* — Kamal Saeed
*Assistant Examiner* — Janet L Coppins
(74) *Attorney, Agent, or Firm* — Sughrue Mion, PLLC

(57) ABSTRACT

[Object] To provide a pharmaceutical product (chemotherapeutic agent) effective in the prevention and treatment of hyperlipidemia, obesity, etc.

[Solving Means] A phenylimidazole compound represented by the following General Formula (1):

(1)

$$R^1-O-\text{[benzene ring substituted with } R^7, R^8, R^2, R^3\text{]}-\text{[imidazole ring with } R^5, R^6, R^4\text{]}$$

wherein, $R^1$ represents a hydrogen atom, a phenyl lower alkyl group optionally having a substituent, or a pyridyl lower alkyl group optionally having a substituent, and the benzene ring and the pyridine ring are optionally substituted with 1 or 2 substituents selected from the group consisting of halogen atoms, cyano group and halogen-substituted lower alkyl groups. One of $R^2$ and $R^3$ represents a hydrogen atom and the other represents a lower alkoxy group. $R^4$ represents a phenyl group optionally having a substituent. $R^5$ and $R^6$ are the same or different, and represent a hydrogen atom or a lower alkyl group. $R^7$ and $R^8$ are the same or different, and represent a hydrogen atom or a lower alkoxy group. However, when $R^1$ represents an unsubstituted phenyl lower alkyl group, $R^2$ represents a lower alkoxy group, $R^3$ represents a hydrogen atom, $R^4$ represents a phenyl group optionally having a substituent, and $R^5$ represents a hydrogen atom, $R^6$ is not a hydrogen atom.

24 Claims, No Drawings

PHENYLIMIDAZOLE COMPOUNDS

CROSS REFERENCE TO RELATED APPLICATIONS

This application is a National Stage of International Application No. PCT/JP2010/051469 filed Feb. 3, 2010, claiming priority based on Japanese Patent Application Nos. 2009-023793 filed Feb. 4, 2009 and 2009-255980 filed Nov. 9, 2009, the contents of all of which are incorporated herein by reference in their entirety.

TECHNICAL FIELD

The present invention relates to a novel phenylimidazole compound.

BACKGROUND ART

Today's society is called a society of gluttony, and the number of people diagnosed with hyperlipidemia, obesity, etc., has been sharply rising. Conditions such as hyperlipidemia, obesity, and the like are extremely dangerous because these conditions can induce diabetes and cause arteriosclerosis and other diseases, such as cardiac infarction and cerebral infarction, which are attributed to arteriosclerosis.

Accordingly, for the purpose of preventing and treating hyperlipidemia, obesity, etc., a variety of studies have been conducted on pharmaceutical products, chemotherapy, and the like for ameliorating these conditions. Chemotherapy used to activate LPL (lipoprotein lipase) and chemotherapeutic agents therefor are examples of such studies. LPL activation is considered to be effective in the prevention and treatment of hyperlipidemia, obesity, etc. (For example, Non-Patent Documents 1 to 6)

PRIOR-ART DOCUMENT

Non-Patent Documents

[Non-Patent Document 1] LPL Activation and Arteriosclerosis: J. Clin. Invest., 92, 411 (1993)
[Non-Patent Document 2] LPL Activation and Cataract: Biol. Pharm. Bull., 19, 1570 (1996)
[Non-Patent Document 3] LPL Activation and Cachexia: Anticancer Research, 19, 4099 (1999)
[Non-Patent Document 4] LPL Activity and Nephrosis: Metabolism, 49, 588 (2000)
[Non-Patent Document 5] LPL Activation and Hyperlipidemia: Diabetes, 44, 414 (1995)
[Non-Patent Document 6] LPL Activation and Obesity: Diabetologia, 43, 875 (2000)

SUMMARY OF THE INVENTION

Object to be Achieved by the Invention

A main object of the present invention is to provide a pharmaceutical product (chemotherapeutic agent) that is effective in the prevention and treatment of hyperlipidemia, obesity, etc.

Means to Achieve the Object

For the purpose of providing a pharmaceutical product (chemotherapeutic agent) effective in the prevention and treatment of hyperlipidemia, obesity, etc., the present inventors have conducted intensive studies to develop a compound having an LPL-activation function, particularly an LPL-activation function that is specific to skeletal muscle. During the course of these studies, the inventors succeeded in synthesizing a phenylimidazole compound represented by General Formula (1) shown below and found that the compound has the desired properties. The present invention was made based on this knowledge.

The present invention provides the following inventions according to Items 1 to 30.

Item 1. A phenylimidazole compound represented by the following General Formula (1):

[Chem. 1]

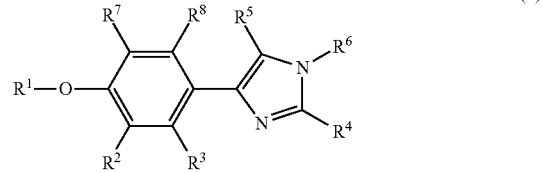

(1)

wherein $R^1$ represents a hydrogen atom, a phenyl lower alkyl group or a pyridyl lower alkyl group, and the benzene ring and the pyridine ring are optionally substituted with 1 or 2 substituents selected from the group consisting of halogen atoms, cyano group and halogen-substituted lower alkyl groups One of $R^2$ and $R^3$ represents a hydrogen atom and the other represents a lower alkoxy group. $R^4$ represents a lower alkyl group, a furyl group, a thienyl group or a phenyl group optionally substituted with 1 or 2 substituents selected from the group consisting of lower alkyl groups, lower alkoxy groups, halogen atoms, carboxyl group, lower alkoxycarbonyl groups and halogen-substituted lower alkyl groups. $R^5$ and $R^6$ are the same or different, and represent a hydrogen atom or a lower alkyl group. $R^7$ and $R^8$ are the same or different, and represent a hydrogen atom or a lower alkoxy group. However, when $R^1$ represents an unsubstituted phenyl lower alkyl group, $R^2$ represents a lower alkoxy group, $R^3$ represents a hydrogen atom, $R^4$ represents an unsubstituted phenyl group or a phenyl group having 1 or 2 halogen-substituted lower alkyl groups, and $R^5$ represents a hydrogen atom, $R^6$ is not a hydrogen atom.

Item 2. The phenylimidazole compound according to Item 1, wherein $R^7$ and $R^8$ represent a hydrogen atom in General Formula (1).

Item 3. The phenylimidazole compound according to Item 1 or 2, wherein $R^4$ represents a thienyl group in General Formula (1).

Item 4. The phenylimidazole compound according to Item 1 or 2, wherein $R^4$ represents a furyl group in General Formula (1).

Item 5. The phenylimidazole compound according to Item 1 or 2, wherein, in General Formula (1), $R^4$ represents a phenyl group optionally substituted with 1 or 2 substituents selected from the group consisting of lower alkyl groups, lower alkoxy groups, halogen atoms, carboxyl group, lower alkoxycarbonyl groups and halogen-substituted lower alkyl groups.

Item 6. The phenylimidazole compound according to Item 1 or 2, wherein, in General Formula (1), $R^1$ is an unsubstituted phenyl lower alkyl group or a phenyl lower alkyl group substituted with 1 or 2 substituents selected from the group consisting of halogen atoms, cyano group and halogen-substituted lower alkyl groups.

Item 7. The phenylimidazole compound according to Item 6, wherein, in General Formula (1), $R^1$ is a group selected from the group consisting of benzyl, 4-cyanobenzyl, 3-cyanobenzyl, 2-cyanobenzyl, 4-chlorobenzyl, 4-trifluoromethylbenzyl, 4-chloro-2-fluorobenzyl and 4-bromo-2-fluorobenzyl.

Item 8. The phenylimidazole compound according to Item 6, wherein, in General Formula (1), $R^1$ is a group selected from the group consisting of benzyl, 4-cyanobenzyl, 3-cyanobenzyl, 2-cyanobenzyl, 4-chlorobenzyl and 4-bromo-2-fluorobenzyl.

Item 9. The phenylimidazole compound according to Item 1, 2 or 6, wherein, in General Formula (1), $R^4$ is a thienyl group, a furyl group or a phenyl group optionally substituted with 1 or 2 substituents selected from the group consisting of lower alkyl groups, lower alkoxy groups, halogen atoms, lower alkoxycarbonyl groups and halogen-substituted lower alkyl groups.

Item 10. The phenylimidazole compound according to Item 1, 2 or 6, wherein, in General Formula (1), $R^4$ is a group selected from the group consisting of 2-thienyl, 3-thienyl, 3-furyl, phenyl, 4-fluorophenyl, 3-fluorophenyl, 3-fluoro-4-methylphenyl, 3,4-difluorophenyl, 4-trifluoromethylphenyl, 3-trifluoromethylphenyl, 2-trifluoromethylphenyl, 4-chlorophenyl, 3-chlorophenyl, 3,4-dichlorophenyl, 3,5-dichlorophenyl, 3-chloro-4-fluorophenyl, 3-methoxyphenyl, 4-methoxyphenyl, 3,4-dimethoxyphenyl, 4-methoxycarbonylphenyl, 4-carboxyphenyl, 4-(1,1-dimethylethyl)phenyl, 1-methylethyl and 4-methylphenyl.

Item 11. The phenylimidazole compound according to Item 10, wherein, in General Formula (1), $R^4$ is a group selected from the group consisting of 2-thienyl, 3-thienyl, 3-furyl, phenyl, 4-fluorophenyl, 3-fluorophenyl, 3,4-difluorophenyl, 4-trifluoromethylphenyl, 3-trifluoromethylphenyl, 2-trifluoromethylphenyl, 4-chlorophenyl, 3-chlorophenyl, 3,4-dichlorophenyl, 3,5-dichlorophenyl, 3-chloro-4-fluorophenyl, 3-methoxyphenyl, 4-methoxycarbonylphenyl, 4-(1,1-dimethylethyl)phenyl, 1-methylethyl and 4-methylphenyl.

Item 12. The phenylimidazole compound according to Item 1 or 2, wherein, in General Formula (1), $R^1$ is a pyridyl lower alkyl group optionally substituted with 1 or 2 substituents selected from the group consisting of halogen atoms, cyano group, and halogen-substituted lower alkyl groups.

Item 13. The phenylimidazole compound according to Item 12, wherein, in General Formula (1), $R^1$ is a group selected from the group consisting of 5-trifluoromethyl-2-pyridylmethyl, 2-pyridylmethyl, 3-pyridylmethyl, 5-chloro-2-pyridylmethyl and 5-cyano-2-pyridylmethyl.

Item 14. The phenylimidazole compound according to Item 1 or 2, wherein, in General Formula (1), $R^1$ is a pyridyl lower alkyl group optionally substituted with a halogen-substituted lower alkyl group.

Item 15. The phenylimidazole compound according to Item 14, wherein, in General Formula (1), $R^1$ is a group selected from the group consisting of 2-pyridylmethyl and 6-trifluoromethyl-3-pyridylmethyl.

Item 16. The phenylimidazole compound according to Item 1 or 2, wherein, in General Formula (1), $R^1$ is a group selected from the group consisting of benzyl, 4-chlorobenzyl and 4-bromo-2-fluorobenzyl, and $R^4$ is a group selected from the group consisting of 4-trifluoromethylphenyl, 4-fluorophenyl, 3,4-difluorophenyl, 4-chlorophenyl, 3,4-dichlorophenyl and 4-methylphenyl.

Item 17. The phenylimidazole compound according to Item 1, selected from the following compounds:

4-[4-(4-bromo-2-fluorobenzyloxy)-3-methoxyphenyl]-2-[4-(trifluoromethyl)phenyl]-1H-imidazole
4-[4-(4-cyanobenzyloxy)-2-methoxyphenyl]-2-[4-(trifluoromethyl)phenyl]-1H-imidazole
4-[4-(4-bromo-2-fluorobenzyloxy)-2-methoxyphenyl]-2-[4-(trifluoromethyl)phenyl]-1H-imidazole
4-[4-(4-chlorobenzyloxy)-2-methoxyphenyl]-2-[4-(trifluoromethyl)phenyl]-1H-imidazole
4-(4-benzyloxy-3-methoxyphenyl)-2-(3-thienyl)-1H-imidazole
4-(4-benzyloxy-2-methoxyphenyl)-2-(4-fluorophenyl)-1H-imidazole
4-(4-benzyloxy-3-methoxyphenyl)-2-(4-fluorophenyl)-5-methyl-1H-imidazole
4-[4-(4-chlorobenzyloxy)-2-methoxyphenyl]-2-(4-fluorophenyl)-1H-imidazole
4-[4-(4-chlorobenzyloxy)-3-methoxyphenyl]-2-[4-(trifluoromethyl)phenyl]-1H-imidazole
4-[4-(4-cyanobenzyloxy)-2-methoxyphenyl]-2-(4-fluorophenyl)-1H-imidazole
4-[4-(4-bromo-2-fluorobenzyloxy)-3-methoxyphenyl]-2-(4-fluorophenyl)-1H-imidazole
4-[4-(4-bromo-2-fluorobenzyloxy)-2-methoxyphenyl]-2-(4-fluorophenyl)-1H-imidazole
4-[4-(4-bromo-2-fluorobenzyloxy)-2-methoxyphenyl]-2-(4-chlorophenyl)-1H-imidazole
4-[4-(4-bromo-2-fluorobenzyloxy)-3-methoxyphenyl]-2-(2-thienyl)-1H-imidazole
4-[4-(4-chlorobenzyloxy)-2-methoxyphenyl]-2-(3-thienyl)-1H-imidazole
4-[4-(4-cyanobenzyloxy)-2-methoxyphenyl]-2-[3-(trifluoromethyl)phenyl]-1H-imidazole
4-[4-(4-bromo-2-fluorobenzyloxy)-2-methoxyphenyl]-2-(4-methylphenyl)-1H-imidazole
4-[4-(4-chlorobenzyloxy)-2-methoxyphenyl]-2-(3,4-difluorophenyl)-1H-imidazole
4-(4-benzyloxy-2-methoxyphenyl)-2-(3,4-difluorophenyl)-1H-imidazole
4-(4-benzyloxy-2-methoxyphenyl)-2-(3,4-dichlorophenyl)-1H-imidazole.

Item 18. The phenylimidazole compound according to Item 1, selected from the following compounds:
4-[4-(4-bromo-2-fluorobenzyloxy)-2-methoxyphenyl]-2-[4-(trifluoromethyl)phenyl]-1H-imidazole
4-[4-(4-chlorobenzyloxy)-2-methoxyphenyl]-2-[4-(trifluoromethyl)phenyl]-1H-imidazole
4-(4-benzyloxy-2-methoxyphenyl)-2-(4-fluorophenyl)-1H-imidazole
4-(4-benzyloxy-3-methoxyphenyl)-2-(4-fluorophenyl)-5-methyl-1H-imidazole
4-[4-(4-chlorobenzyloxy)-2-methoxyphenyl]-2-(4-fluorophenyl)-1H-imidazole
4-[4-(4-bromo-2-fluorobenzyloxy)-2-methoxyphenyl]-2-(4-fluorophenyl)-1H-imidazole
4-[4-(4-bromo-2-fluorobenzyloxy)-2-methoxyphenyl]-2-(4-chlorophenyl)-1H-imidazole
4-[4-(4-bromo-2-fluorobenzyloxy)-2-methoxyphenyl]-2-(4-methylphenyl)-1H-imidazole
4-[4-(4-chlorobenzyloxy)-2-methoxyphenyl]-2-(3,4-difluorophenyl)-1H-imidazole
4-(4-benzyloxy-2-methoxyphenyl)-2-(3,4-difluorophenyl)-1H-imidazole
4-(4-benzyloxy-2-methoxyphenyl)-2-(3,4-dichlorophenyl)-1H-imidazole
4-[4-(4-cyanobenzyloxy)-2-methoxyphenyl]-2-(4-fluorophenyl)-1H-imidazole.

Item 19. A pharmaceutical composition containing, as an active ingredient, the compound according to any one of Items 1 to 18.

Item 20. An LPL activator containing, as an active ingredient, the compound according to any one of Items 1 to 18.

Item 21. An agent for preventing and treating hyperlipidemia containing, as an active ingredient, the compound according to any one of Items 1 to 18.

Item 22. An anti-arteriosclerotic agent containing, as an active ingredient, the compound according to any one of Items 1 to 18.

Item 23. An anti-obesity agent containing, as an active ingredient, the compound according to any one of Items 1 to 18.

Item 24. A method of activating LPL, comprising administering an effective amount of the compound according to any one of Items 1 to 18.

Item 25. A method of preventing or treating hyperlipidemia, comprising administering an effective amount of the compound according to any one of Items 1 to 18.

Item 26. A method of preventing or treating arteriosclerosis, comprising administering an effective amount of the compound according to any one of Items 1 to 18.

Item 27. A method of preventing or treating obesity, comprising administering an effective amount of the compound according to any one of Items 1 to 18.

Item 28. Use of the compound according to any one of Items 1 to 18 as a medicine.

Item 29. Use of the compound according to any one of Items 1 to 18 for producing an LPL activator.

Item 30. The compound according to any one of Items 1 to 18 for use in activating LPL.

Effects of the Invention

The phenylimidazole compound of the present invention has a lipoprotein lipase (LPL) activating action, and is effective as an LPL activator in the prevention and treatment of hyperlipidemia, arteriosclerosis, obesity, etc.

BEST MODE FOR CARRYING OUT THE INVENTION

Hereinbelow, the phenylimidazole compound of the present invention is described in detail.

Each group described in General Formula (1) and elsewhere in the present specification is described more specifically as follows. In the present specification, the term "lower" used for each group containing a carbon refers to a group "having 1 to 6 carbons".

Examples of lower alkyl groups include straight or branched $C_{1-6}$ alkyl groups such as methyl, ethyl, propyl, 1-methylethyl, butyl, 2-methylpropyl, 1,1-dimethylethyl, pentyl, hexyl, etc.

Examples of lower alkoxy groups include $C_{1-6}$ alkoxy groups such as methoxy, ethoxy, propoxy, 1-methylethoxy, butoxy, 2-methylpropoxy, 1,1-dimethylethoxy, pentyloxy, hexyloxy, etc.

Examples of halogen atoms include fluorine, chlorine, bromine, iodine, etc.

Examples of furyl groups include 2-furyl, 3-furyl, etc.

Examples of thienyl groups include 2-thienyl, 3-thienyl, etc.

Examples of halogen-substituted lower alkyl groups include a halogenoalkyl group which has a straight or branched $C_{1-6}$ alkyl group substituted with at least one halogen atom selected from the group consisting of fluorine, chlorine, bromine and iodine atoms. A preferable example thereof is a perhalogenoalkyl group, and a particularly preferable example thereof is a perfluoroalkyl group. Specific examples thereof include trifluoromethyl, pentafluoroethyl, heptafluoropropyl, nonafluorobutyl, undecafluoropentyl, tridecafluorohexyl, etc.

Examples of lower alkoxycarbonyl groups include a straight or branched $C_{1-6}$ alkoxy carbonyl group such as methoxycarbonyl, ethoxycarbonyl, propoxycarbonyl, 1-methylethoxycarbonyl, butoxycarbonyl, 2-methylpropoxycarbonyl, 1,1-dimethylethoxycarbonyl, pentyloxycarbonyl, hexyloxycarbonyl, etc.

Examples of phenyl lower alkyl groups optionally substituted with 1 or 2 substituents selected from the group consisting of halogen atoms, cyano group and halogen-substituted lower alkyl groups include the following: benzyl, 1-phenylethyl, 2-phenylethyl, 3-phenylpropyl, 4-phenylbutyl, 5-phenylpentyl, 6-phenylhexyl, 2-chlorobenzyl, 3-chlorobenzyl, 4-chlorobenzyl, 2-bromobenzyl, 3-bromobenzyl, 4-bromobenzyl, 2-iodobenzyl, 3-iodobenzyl, 4-iodobenzyl, 2-fluorobenzyl, 3-fluorobenzyl, 4-fluorobenzyl, 2,4-dichlorobenzyl, 2,3-dichlorobenzyl, 3,5-dichlorobenzyl, 3,4-dichlorobenzyl, 2,5-dichlorobenzyl, 2,6-dichlorobenzyl, 2,4-difluorobenzyl, 2,4-dibromobenzyl, 2,4-diiodobenzyl, 4-bromo-2-fluorobenzyl, 2-bromo-4-fluorobenzyl, 4-bromo-2-chlorobenzyl, 4-chloro-2-fluorobenzyl, 2-cyanobenzyl, 3-cyanobenzyl, 4-cyanobenzyl, 2,4-dicyanobenzyl, 3,5-dicyanobenzyl, 4-bromo-2-cyanobenzyl, 2-bromo-4-cyanobenzyl, 4-chloro-2-cyanobenzyl, 2-chloro-4-cyanobenzyl, 4-bromo-2-cyanobenzyl, 2-bromo-4-cyanobenzyl, 4-fluoro-2-cyanobenzyl, 2-fluoro-4-cyanobenzyl, 1-(4-chlorophenyl)ethyl, 2-(4-chlorophenyl)ethyl, 3-(4-chlorophenyl)propyl, 4-(4-chlorophenyl)butyl, 5-(4-chlorophenyl)pentyl, 6-(4-chlorophenyl)hexyl, 1-(4-cyanophenyl)ethyl, 2-(4-cyanophenyl)ethyl, 3-(4-cyanophenyl)propyl, 4-(4-cyanophenyl)butyl, 5-(4-cyanophenyl)pentyl, 6-(4-cyanophenyl)hexyl, 1-(4-bromo-2-fluorophenyl)ethyl, 2-(4-bromo-2-fluorophenyl)ethyl, 3-(4-bromo-2-fluorophenyl)propyl, 4-(4-bromo-2-fluorophenyl)butyl, 5-(4-bromo-2-fluorophenyl)pentyl, 6-(4-bromo-2-fluorophenyl)hexyl, 2-trifluoromethylbenzyl, 3-trifluoromethylbenzyl, 4-trifluoromethylbenzyl, 1-(4-trifluoromethylphenyl)ethyl, 2-(4-trifluoromethylphenyl)ethyl, 3-(4-trifluoromethylphenyl)propyl, 4-(4-trifluoromethylphenyl)butyl, 5-(4-trifluoromethylphenyl)pentyl, 6-(4-trifluoromethylphenyl)hexyl, 2-bromo-4-trifluoromethylbenzyl, 2-cyano-4-trifluoromethylbenzyl, etc.

Examples of pyridyl lower alkyl groups optionally substituted with 1 or 2 substituents selected from the group consisting of halogen atoms, cyano group and halogen-substituted lower alkyl groups include the following: 2-pyridylmethyl, 3-pyridylmethyl, 4-pyridylmethyl, (3-trifluoromethyl-2-pyridyl)methyl, (4-trifluoromethyl-2-pyridyl)methyl, (5-trifluoromethyl-2-pyridyl)methyl, (6-trifluoromethyl-2-pyridyl)methyl, (2-trifluoromethyl-3-pyridyl)methyl, (4-trifluoromethyl-3-pyridyl)methyl, (5-trifluoromethyl-3-pyridyl)methyl, (6-trifluoromethyl-3-pyridyl)methyl, (2-trifluoromethyl-4-pyridyl)methyl, (3-trifluoromethyl-4-pyridyl)methyl, (5-pentafluoroethyl-2-pyridyl)methyl, (5-heptafluoropropyl-2-pyridyl)methyl, (5-nonafluoro-butyl-2-pyridyl)methyl, (5-undecafluoropentyl-2-pyridyl)methyl, (5-tridecafluorohexyl-2-pyridyl)methyl, 1-(5-trifluoromethyl-2-pyridyl)ethyl, 2-(5-trifluoromethyl-2-pyridyl)ethyl, 3-(5-trifluoromethyl-2-pyridyl)propyl, 4-(5-trifluoromethyl-2-pyridyl)butyl, 5-(5-trifluoromethyl-2-pyridyl)pentyl, 6-(5-trifluoromethyl-2-pyridyl)hexyl, (3-bromo-2-pyridyl)methyl, (4-bromo-2- pyridyl)methyl, (5-bromo-2-pyridyl)methyl, (6-bromo-2-pyridyl)methyl, (2-bromo-3-pyridyl)methyl, (4-bromo-3-pyridyl)methyl, (5-bromo-3-pyridyl)methyl, (6-bromo-3-pyridyl)methyl, (2-bromo-4-pyridyl)methyl, (3-bromo-4-pyridyl)methyl, (5-chloro-2-pyridyl)methyl, (6-chloro-3-pyridyl)methyl, (5-fluoro-2-pyridyl)methyl, (6-fluoro-3-pyridyl)methyl, (3-cyano-2-pyridyl)methyl, (4-cyano-2-pyridyl)methyl, (5-cyano-2-pyridyl)methyl, (6-cyano-2-pyridyl)methyl, (2-cyano-3-pyridyl)methyl, (4-cyano-3-pyridyl)methyl, (5-cyano-3-pyridyl)methyl, (6-cyano-3-pyridyl)methyl, (2-cyano-4-pyridyl)methyl, (3-cyano-4-pyridyl)methyl, 1-(5-chloro-2-pyridyl)ethyl, 2-(5-chloro-2-pyridyl)ethyl, 3-(5-chloro-2-pyridyl)propyl, 4-(5-chloro-2-pyridyl)butyl, 5-(5-chloro-2-pyridyl)pentyl, 6-(5-chloro-2-pyridy)hexyl, etc.

Examples of phenyl groups optionally substituted with 1 or 2 substituents selected from the group consisting of lower alkyl groups, lower alkoxy groups, halogen atoms, carboxyl group, lower alkoxycarbonyl groups and halogen-substituted lower alkyl groups include the following in addition to the phenyl group: 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-fluorophenyl, 3-fluorophenyl, 4-fluorophenyl, 3,4-difluorophenyl, 2,4-dichlorophenyl, 2,3-dichlorophenyl, 3,5-dichlorophenyl, 3,4-dichlorophenyl, 2,5-dichlorophenyl, 2,6-dichlorophenyl, 2,4-difluorophenyl, 2,4-dibromophenyl, 3,4-dibromophenyl, 2,4-diiodophenyl, 4-bromo-2-fluorophenyl, 2-bromo-4-fluorophenyl, 4-bromo-2-chlorophenyl, 3-chloro-4-fluorophenyl, 2-methylphenyl, 3-methylphenyl, 4-methylphenyl, 4-ethylphenyl, 4-propylphenyl, 4-(1-methylethyl)phenyl, 4-butylphenyl, 4-(2-methylpropyl)phenyl, 4-(1,1-dimethylethyl)phenyl, 4-pentylphenyl, 4-hexylphenyl, 2,4-dimethylphenyl, 2,3-dimethylphenyl, 3,5-dimethylphenyl, 3,4-dimethylphenyl, 2,5-dimethylphenyl, 2,6-dimethylphenyl, 2-methoxyphenyl, 3-methoxyphenyl, 4-methoxyphenyl, 4-ethoxyphenyl, 4-propoxyphenyl, 4-(1-methylethoxy)phenyl, 4-butoxyphenyl, 4-(2-methylpropoxy)phenyl, 4-(1,1-dimethylethoxy)phenyl, 4-pentyloxyphenyl, 4-hexyloxyphenyl, 2,4-dimethoxyphenyl, 2,3-dimethoxyphenyl, 3,5-dimethoxyphenyl, 3,4-dimethoxyphenyl, 2,5-dimethoxyphenyl, 2,6-dimethoxyphenyl, 2-trifluoromethylphenyl, 3-trifluoromethylphenyl, 4-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 2,4-bistrifluoromethylphenyl, 2,3-bistrifluoromethylphenyl, 3,5-bistrifluoromethylphenyl, 3,4-bistrifluoromethylphenyl, 2,5-bistrifluoromethylphenyl, 2,6-bistrifluoromethylphenyl, 4-methoxy-2-methylphenyl, 4-methoxy-3-methylphenyl, 3-methoxy-5-methylphenyl, 4-chloro-2-methylphenyl, 4-chloro-3-methylphenyl, 3-chloro-5-methylphenyl, 3-fluoro-5-methylphenyl, 3-fluoro-4-methylphenyl, 3-bromo-5-methylphenyl, 3-iodo-5-methylphenyl, 2-methyl-4-trifluoromethylphenyl, 3-methyl-4-trifluoromethylphenyl, 3-methyl-5-trifluoromethylphenyl, 2-chloro-4-methoxyphenyl, 3-chloro-4-methoxyphenyl, 3-chloro-5-methoxyphenyl, 4-methoxy-2-trifluoromethylphenyl, 4-methoxy-3-trifluoromethylphenyl, 3-methoxy-5-trifluoromethylphenyl, 4-chloro-2-trifluoromethylphenyl, 4-chloro-3-trifluoromethylphenyl, 3-chloro-5-trifluoromethylphenyl, 2-carboxyphenyl, 3-carboxyphenyl, 4-carboxyphenyl, 2-methoxycarbonylphenyl, 3-methoxycarbonylphenyl, 4-methoxycarbonylphenyl, 4-ethoxycarbonylphenyl, 4-propoxycarbonylphenyl, 4-butoxycarbonylphenyl, 4-pentyloxycarbonylphenyl, 4-hexyloxycarbonylphenyl, etc.

In General Formula (1), preferable $R^1$ is an unsubstituted phenyl lower alkyl group or a phenyl lower alkyl group substituted with 1 or 2 substituents selected from the group consisting of halogen atoms, cyano group and halogen-substituted lower alkyl groups. Specific examples of preferable $R^1$ include benzyl, 4-cyanobenzyl, 3-cyanobenzyl, 2-cyanobenzyl, 4-chlorobenzyl, 4-trifluoromethylbenzyl, 4-chloro-2-fluorobenzyl and 4-bromo-2-fluorobenzyl, etc. Specific examples of more preferable $R^1$ include benzyl, 4-cyanobenzyl, 3-cyanobenzyl, 2-cyanobenzyl, 4-chlorobenzyl, 4-bromo-2-fluorobenzyl, etc.

Another preferable $R^1$ is a pyridyl lower alkyl group optionally substituted with 1 or 2 substituents selected from the group consisting of halogen atoms, cyano group, and halogen-substituted lower alkyl groups. Specific examples of preferable $R^1$ include 5-trifluoromethyl-2-pyridylmethyl, 2-pyridylmethyl, 3-pyridylmethyl, 5-chloro-2-pyridylmethyl, 5-cyano-2-pyridylmethyl, etc.

Another preferable $R^1$ is a pyridyl lower alkyl group optionally substituted with a halogen-substituted lower alkyl group. Specific examples of preferable $R^1$ include 2-pyridylmethyl, 6-trifluoromethyl-3-pyridylmethyl, etc.

In General Formula (1), preferable $R^4$ is a furyl group, a thienyl group or a phenyl group optionally substituted with 1 or 2 substituents selected from the group consisting of lower alkyl groups, lower alkoxy groups, halogen atoms, carboxyl group, lower alkoxycarbonyl groups and halogen-substituted lower alkyl groups. More preferable $R^4$ is a furyl group, a thienyl group or a phenyl group optionally substituted with 1 or 2 substituents selected from the group consisting of lower alkyl groups, lower alkoxy groups, halogen atoms, lower alkoxycarbonyl groups and halogen-substituted lower alkyl groups.

Specific examples of preferable $R^4$ include 2-thienyl, 3-thienyl, 3-furyl, phenyl, 4-fluorophenyl, 3-fluorophenyl, 3-fluoro-4-methylphenyl 3,4-difluorophenyl, 4-trifluoromethylphenyl, 3-trifluoromethylphenyl, 2-trifluoromethylphenyl, 4-chlorophenyl, 3-chlorophenyl, 3,4-dichlorophenyl, 3,5-dichlorophenyl, 3-chloro-4-fluorophenyl, 3-methoxyphenyl, 4-methoxyphenyl, 3,4-dimethoxyphenyl 4-methoxycarbonylphenyl, 4-carboxyphenyl, 4-(1,1-dimethylethyl)phenyl, 1-methylethyl, 4-methylphenyl, etc. Specific examples of more preferable $R^4$ include 2-thienyl, 3-thienyl, 3-furyl, phenyl, 4-fluorophenyl, 3-fluorophenyl, 3,4-difluorophenyl, 4-trifluoromethylphenyl, 3-trifluoromethylphenyl, 2-trifluoromethylphenyl, 4-chlorophenyl, 3-chlorophenyl, 3,4-dichlorophenyl, 3,5-dichlorophenyl, 3-chloro-4-fluorophenyl, 3-methoxyphenyl, 4-methoxycarbonylphenyl, 4-(1,1-dimethylethyl)phenyl, 1-methylethyl, 4-methylphenyl, etc.

In General Formula (1), preferable $R^4$ and $R^5$ are hydrogen atoms.

In General Formula (1), preferable $R^7$ and $R^8$ are hydrogen atoms.

A preferable phenylimidazole compound represented by General Formula (1) is a compound wherein $R^1$ is a group selected from the group consisting of benzyl, 4-chlorobenzyl and 4-bromo-2-fluorobenzyl; and $R^4$ is a group selected from the group consisting of 4-trifluoromethylphenyl, 4-fluorophenyl, 3,4-difluorophenyl, 4-chlorophenyl, 3,4-dichlorophenyl and 4-methylphenyl.

Specific examples of a more preferable phenylimidazole compound represented by General Formula (1) include the following compounds:

4-[4-(4-bromo-2-fluorobenzyloxy)-3-methoxyphenyl]-2-[4-(trifluoromethyl)phenyl]-1H-imidazole
4-[4-(4-cyanobenzyloxy)-2-methoxyphenyl]-2-[4-(trifluoromethyl)phenyl]-1H-imidazole
4-[4-(4-bromo-2-fluorobenzyloxy)-2-methoxyphenyl]-2-[4-(trifluoromethyl)phenyl]-1H-imidazole
4-[4-(4-chlorobenzyloxy)-2-methoxyphenyl]-2-[4-(trifluoromethyl)phenyl]-1H-imidazole
4-(4-benzyloxy-3-methoxyphenyl)-2-(3-thienyl)-1H-imidazole
4-(4-benzyloxy-2-methoxyphenyl)-2-(4-fluorophenyl)-1H-imidazole
4-(4-benzyloxy-3-methoxyphenyl)-2-(4-fluorophenyl)-5-methyl-1H-imidazole
4-[4-(4-chlorobenzyloxy)-2-methoxyphenyl]-2-(4-fluorophenyl)-1H-imidazole
4-[4-(4-chlorobenzyloxy)-3-methoxyphenyl]-2-[4-(trifluoromethyl)phenyl]-1H-imidazole
4-[4-(4-cyanobenzyloxy)-2-methoxyphenyl]-2-(4-fluorophenyl)-1H-imidazole
4-[4-(4-bromo-2-fluorobenzyloxy)-3-methoxyphenyl]-2-(4-fluorophenyl)-1H-imidazole
4-[4-(4-bromo-2-fluorobenzyloxy)-2-methoxyphenyl]-2-(4-fluorophenyl)-1H-imidazole
4-[4-(4-bromo-2-fluorobenzyloxy)-2-methoxyphenyl]-2-(4-chlorophenyl)-1H-imidazole
4-[4-(4-bromo-2-fluorobenzyloxy)-3-methoxyphenyl]-2-(2-thienyl)-1H-imidazole
4-[4-(4-chlorobenzyloxy)-2-methoxyphenyl]-2-(3-thienyl)-1H-imidazole
4-[4-(4-cyanobenzyloxy)-2-methoxyphenyl]-2-[3-(trifluoromethyl)phenyl]-1H-imidazole
4-[4-(4-bromo-2-fluorobenzyloxy)-2-methoxyphenyl]-2-(4-methylphenyl)-1H-imidazole
4-[4-(4-chlorobenzyloxy)-2-methoxyphenyl]-2-(3,4-difluorophenyl)-1H-imidazole
4-(4-benzyloxy-2-methoxyphenyl)-2-(3,4-difluorophenyl)-1H-imidazole
4-(4-benzyloxy-2-methoxyphenyl)-2-(3,4-dichlorophenyl)-1H-imidazole.

Specific examples of a particularly preferable phenylimidazole compound represented by General Formula (1) include the following compounds:
4-[4-(4-bromo-2-fluorobenzyloxy)-2-methoxyphenyl]-2-[4-(trifluoromethyl)phenyl]-1H-imidazole
4-[4-(4-chlorobenzyloxy)-2-methoxyphenyl]-2-[4-(trifluoromethyl)phenyl]-1H-imidazole
4-(4-benzyloxy-2-methoxyphenyl)-2-(4-fluorophenyl)-1H-imidazole
4-(4-benzyloxy-3-methoxyphenyl)-2-(4-fluorophenyl)-5-methyl-1H-imidazole
4-[4-(4-chlorobenzyloxy)-2-methoxyphenyl]-2-(4-fluorophenyl)-1H-imidazole
4-[4-(4-bromo-2-fluorobenzyloxy)-2-methoxyphenyl]-2-(4-fluorophenyl)-1H-imidazole
4-[4-(4-bromo-2-fluorobenzyloxy)-2-methoxyphenyl]-2-(4-chlorophenyl)-1H-imidazole
4-[4-(4-bromo-2-fluorobenzyloxy)-2-methoxyphenyl]-2-(4-methylphenyl)-1H-imidazole
4-[4-(4-chlorobenzyloxy)-2-methoxyphenyl]-2-(3,4-difluorophenyl)-1H-imidazole
4-(4-benzyloxy-2-methoxyphenyl)-2-(3,4-difluorophenyl)-1H-imidazole
4-(4-benzyloxy-2-methoxyphenyl)-2-(3,4-dichlorophenyl)-1H-imidazole
4-[4-(4-cyanobenzyloxy)-2-methoxyphenyl]-2-(4-fluorophenyl)-1H-imidazole.

Method of Producing Compound (1) of the Present Invention

The phenylimidazole compound of the present invention can be produced by various methods.
A preferable example thereof is as follows.

[Reaction Scheme-1]

[Chem. 2]

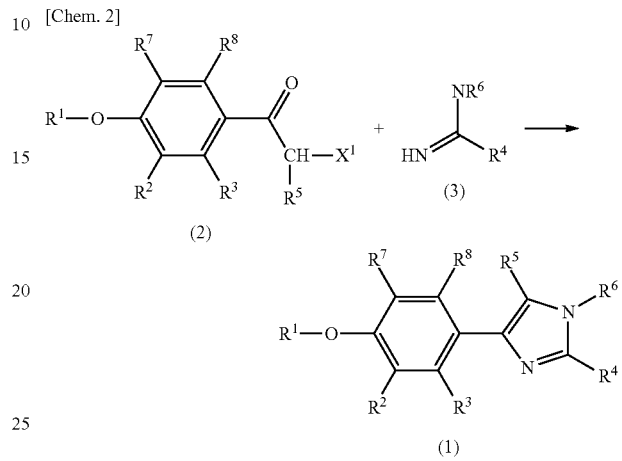

wherein, $R^1$, $R^2$, $R^3$, $R^4$, $R^5$, $R^6$, $R^7$ and $R^8$ are as defined above. $X^1$ represents a halogen atom.

As shown in Reaction Scheme-1 described above, compound (1) of the present invention can be produced through cyclization of compound (2) and compound (3).

The cyclization reaction is carried out by reacting substantially equimolar amounts of compound (2) and compound (3) in an inert solvent such as tetrahydrofuran (THF), 1,4-dioxane, water, or a mixture of these, in the presence of an alkali such as sodium hydrogen carbonate, potassium hydrogen carbonate, sodium carbonate, etc., at room temperature to 100° C. for 0.5 to 10 hours. 1 to 5 moles of alkali are used per mole of compound (2).

Compound (2), which is used as a starting material in Reaction Scheme-1, can be obtained by the halogenation reaction shown in Reaction Scheme-2 below.

[Reaction Scheme-2]

[Chem. 3]

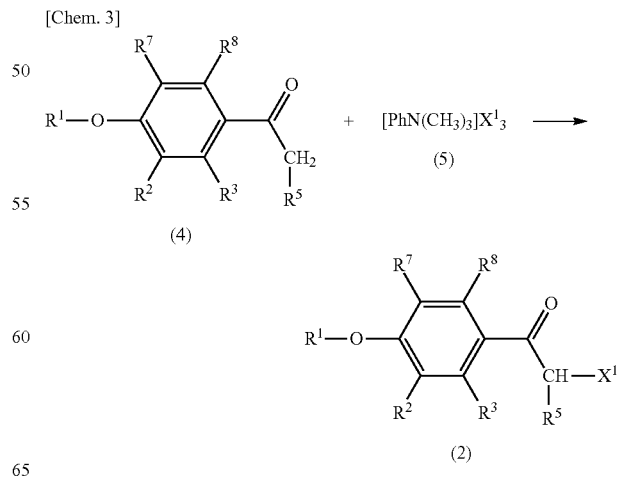

wherein, $R^1$, $R^2$, $R^3$, $R^5$, $R^7$, $R^8$ and $X^1$ are as defined above.

The desired compound (2) can be obtained by reacting compound (4) and trimethylphenylammonium trihalide (5), for example, in an inert solvent such as tetrahydrofuran (THF), 1,4-dioxane, etc., at 0° C. to 50° C. for 5 to 20 hours. 1 to 1.3 moles of trimethylphenylammonium trihalide (5) are used per mole of compound (4).

Further, in Reaction Scheme-2, compound (4a) included in compound (4) used as a starting material is a compound wherein $R^1$ is a phenyl lower alkyl group optionally substituted with 1 or 2 substituents selected from the group consisting of halogen atoms, cyano group and halogen-substituted lower alkyl groups; and compound (4b) included in compound (4) is a compound wherein $R^1$ is a pyridyl lower alkyl group optionally substituted with 1 or 2 substituents selected from the group consisting of halogen atoms, cyano group and halogen-substituted lower alkyl groups. These compounds (4a) and (4b) can be produced by the methods shown in Reaction Scheme-3 and Reaction Scheme-4 below, respectively.

[Reaction Scheme-3]

[Chem. 4]

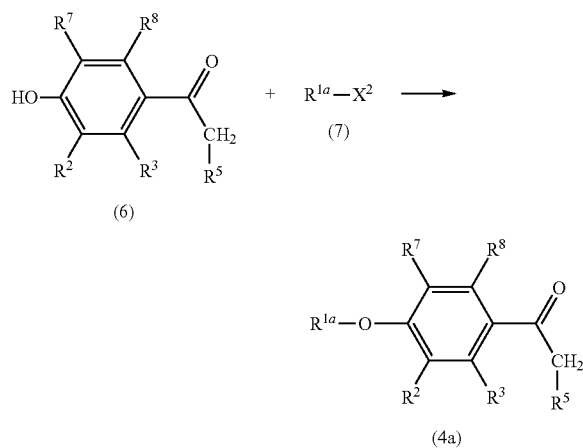

wherein, $R^{1a}$ represents a phenyl lower alkyl group optionally substituted with 1 or 2 substituents selected from the group consisting of halogen atoms, cyano group and halogen-substituted lower alkyl groups, or a pyridyl lower alkyl group optionally substituted with 1 or 2 substituents selected from the group consisting of halogen atoms, cyano group and halogen-substituted lower alkyl groups; and $R^2$, $R^3$, $R^5$, $R^7$ and $R^8$ are as defined above. $X^2$ represents a halogen atom.

The above-mentioned known compound (6) can be converted to compound (4a) by reacting it with halide (7). The reaction is carried out in an inert solvent such as N,N-dimethylformamide (DMF), N,N-dimethylacetamide (DMA), dimethyl sulfoxide (DMSO), etc., in the presence of an alkali such as potassium carbonate, sodium carbonate, etc., and is completed at room temperature to 100° C. in about 5 to about 30 hours. 1 to 2 moles of halide (7) are used per mole of compound (6), and 1 to 3 moles of alkali are used per mole of compound (6).

[Reaction Scheme-4]

[Chem. 5]

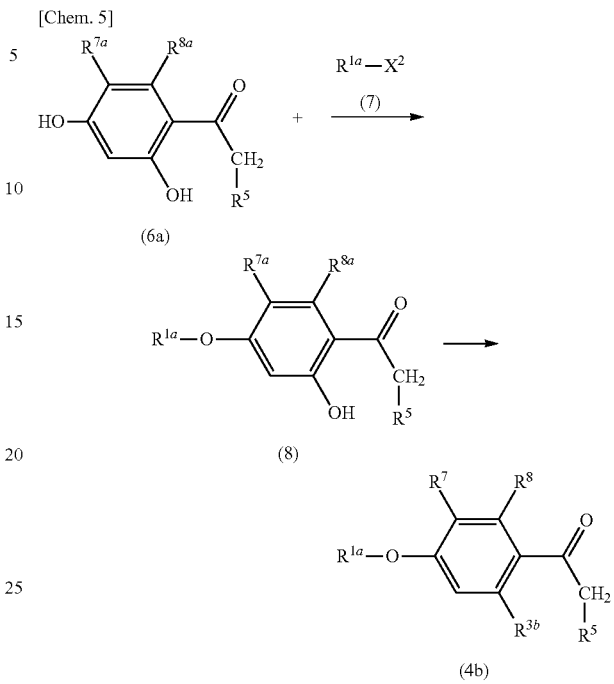

wherein, $R^{3b}$ represents a lower alkoxy group, $R^{7a}$ and $R^{8a}$ are the same or different and represent a hydrogen atom or a hydroxy group, and $R^{1a}$, $R^2$, $R^3$, $R^5$, $R^7$, $R^8$ and $X^2$ are as defined above.

The above-mentioned known compound (6a) is reacted with halide (7), converted into compound (8), and then alkylated. Thereby, compound (4b) can be induced from compound (6a). The reaction of compound (6a) with halide (7) is carried out under the same reaction conditions as the reaction shown in the above Reaction Scheme-3.

The alkylation reaction of the resulting compound (8) is carried out in an inert solvent such as N,N-dimethylformamide (DMF), N,N-dimethylacetamide (DMA), dimethyl sulfoxide (DMSO), etc., in the presence of an alkali such as potassium carbonate, sodium carbonate, etc., using a lower alkyl halide such as iodomethane, iodoethane, 1-iodopropane, 1-iodobutane, 1-iodopentane, 1-iodohexane, etc., and is completed at 0° C. to 50° C. in about 10 to about 100 hours. 1 to 3 equivalents of alkali are used per mole of compound (8), and 1 to 2 equivalents of lower alkyl halide are used per mole of compound (8).

Some of the compounds of the present invention are capable of forming pharmacologically acceptable acid addition salts, for example, hydrochloride, nitrate, sulfate, hydrobromide, phosphate, carbonate, acetate, lactate, citrate, etc. These acid addition salts can also be produced according to known methods. The present invention also includes these acid addition salts.

Note that some of the compounds of the present invention may include optical isomers having a carbon atom as an asymmetric center. The present invention includes all racemates that are mixtures of such optical isomers, and optically active forms (i.e., optical isomers). The above-mentioned optical isomers can be separated using various known separation methods.

The desired compound in each process shown in each Reaction Scheme described above and the compound of the present invention can be easily isolated and purified by conventional separation means. Examples of such separation means include adsorption chromatography, preparative thin-layer chromatography, recrystallization, solvent extraction, etc.

The compound of the present invention (including a salt thereof; the same applies below) has a lipoprotein lipase (LPL) activating action, and is effective as an LPL activator in the prevention and treatment of hyperlipidemia, arteriosclerosis, obesity, etc. Accordingly, the present invention also provides an agent for preventing and treating hyperlipidemia, an anti-arteriosclerotic agent, an anti-obesity agent, and the like.

The present invention also provides a pharmaceutical composition containing the compound of the present invention. Such a pharmaceutical composition is usually used in the form of a general pharmaceutical preparation. Examples of pharmaceutically acceptable carriers used for the pharmaceutical preparation of the present invention include fillers, extenders, binders, wetting agents, disintegrants, surfactants, lubricants, and like diluents and excipients that are usually used according to the usage of the pharmaceutical preparations. These carriers are suitably selected according to the unit dosage form of the resulting pharmaceutical preparations.

A variety of unit dosage forms can be suitably selected for the above-mentioned pharmaceutical preparation, depending on the therapeutic purpose. Typical examples are tablets, pills, powders, solutions, suspensions, emulsions, granules, capsules, suppositories, injections (solutions, suspensions, etc.), ointments, etc.

To form tablets, the following, for example, may be used as the above-mentioned pharmaceutically acceptable carriers: lactose, sucrose, sodium chloride, glucose, urea, starch, calcium carbonate, kaolin, crystalline cellulose, silicic acid, potassium phosphate and other excipients; water, ethanol, propanol, simple syrup, glucose solutions, starch solutions, gelatin solutions, carboxymethylcellulose, hydroxypropylcellulose, methylcellulose, polyvinylpyrrolidone and other binders; carboxymethylcellulose sodium, carboxymethylcellulose calcium, low-substituted hydroxypropyl cellulose, dry starch, sodium alginate, agar powder, laminarin powder, sodium hydrogen carbonate, calcium carbonate and other disintegrators; fatty acid esters of polyoxyethylene sorbitan, sodium lauryl sulfate, stearic acid monoglycerides and other surfactants; sucrose, stearin, cacao butter, hydrogenated oils and other disintegration inhibitors; quaternary ammonium bases, sodium lauryl sulfate and other absorption promoters; glycerole, starch and other wetting agents; starch, lactose, kaolin, bentonite, colloidal silicic acid and other adsorbents; purified talc, stearate, boric acid powder, polyethylene glycol and other lubricants, etc. Further, such tablets may be coated with typical coating materials as required, to prepare, for example, sugar-coated tablets, gelatin-coated tablets, enteric-coated tablets, film-coated tablets, double- or multi-layered tablets, etc.

To form pills, the following, for example, may be used as the pharmaceutically acceptable carriers: glucose, lactose, starch, cacao butter, hydrogenated vegetable oils, kaolin, talc and other excipients; gum arabic powder, tragacanth powder, gelatin, ethanol and other binders; laminarin, agar and other disintegrators, etc.

To form suppositories, the following, for example, may be used as the pharmaceutically acceptable carriers: polyethylene glycol, cacao butter, higher alcohols, esters of higher alcohols, gelatin, semi synthetic glycerides, etc.

Capsules are prepared according to known methods, typically by mixing the compounds of the present invention with the above-mentioned pharmaceutically acceptable carriers and loading the mixture into a hard gelatin capsule, soft gelatin capsule or the like.

To prepare injections such as solutions, emulsions, suspensions, etc., the injections are sterilized and preferably made isotonic to blood. To form such injections, the following, for example, may be used as diluents: water, ethanol, macrogol, propylene glycol, ethoxylated isostearyl alcohol, polyoxylated isostearyl alcohol, fatty acid esters of polyoxyethylene sorbitan, etc. In this case, the pharmaceutical preparation may contain sodium chloride, glucose or glycerol in an amount sufficient to prepare an isotonic solution, and may also contain typical solubilizers, buffers, soothing agents, etc.

To form ointments such as pastes, creams, gels, etc., the following, for example, may be used as diluents: white petrolatum, paraffin, glycerol, cellulose derivatives, polyethylene glycol, silicone, bentonite, etc.

Further, the preparation of the present invention may contain, if necessary, coloring agents, preservatives, fragrances, flavors, sweetening agents, etc., and/or other medicines and be prepared as a pharmaceutical preparation.

The amount of the compounds (active ingredient compounds) of the present invention to be contained in the preparation of the present invention is not particularly limited, and is suitably selected from a wide range. Generally, the proportion thereof in the pharmaceutical preparation is about 0.5 to about 90 wt. %, preferably about 1 to about 85 wt. %.

The route of administration of the pharmaceutical preparation described above is not particularly limited, and is determined by the form of the preparation, the patient's age, gender and other conditions, the severity of the disease, etc. For example, tablets, pills, solutions, suspensions, emulsions, granules and capsules are administered orally. Injections are administered intravenously, intramuscularly, intracutaneously, subcutaneously or intraperitoneally, alone or in combination with typical injection transfusions such as glucose solutions, amino acid solutions or the like. Suppositories are administered intrarectally.

The dosage of the pharmaceutical preparation described above is suitably selected according to the method of use, the patient's age, gender and other conditions, the severity of the disease, etc. The amount of the compounds of the present invention, i.e., the active ingredients, is usually about 0.5 to about 20 mg, preferably about 1 to about 10 mg per kg body weight per human adult per day. The preparation can be administered once a day, or 2 to 4 times a day in separate doses.

Further, the present invention is a method of activating LPL in patients in need of LPL activation treatment, the method including administering an effective amount of at least one compound of the present invention to the patients.

Additionally, the present invention provides a method of preventing or treating hyperlipidemia in patients in need of prevention or treatment of hyperlipidemia, the method including administering an effective amount of at least one compound of the present invention to the patients.

Additionally, the present invention provides a method of preventing or treating arteriosclerosis for patients in need of prevention or treatment of arteriosclerosis, the method including administering an effective amount of at least one compound of the present invention to the patients.

Further, the present invention provides a method of preventing or treating obesity for patients in need of obesity treatment, the method including administering an effective amount of at least one compound of the present invention to the patients.

Furthermore, the present invention provides the use of the compounds of the present invention for producing an LPL-activating composition; the use of the compounds of the present invention for producing a composition for preventing or treating hyperlipidemia; and the use of the compounds of the present invention for producing an anti-obesity composition.

EXAMPLE

Hereinafter, the present invention is described in more detail with reference to reference examples, examples, etc. However, the present invention is not limited thereto.

Reference Example 1

Production of 2-bromo-1-[4-(4-bromo-2-fluorobenzyloxy)-3-methoxyphenyl]ethanone 1-(4-hydroxy-3-methoxyphenyl)ethanone (25.0 g, 0.15 mol) and potassium carbonate (15.4 g, 0.11 mol) were added to DMF (80 mL). 4-bromo-1-(bromomethyl)-2-fluorobenzene (50.2 g, 0.19 mol) was added to the mixture, and the mixture was stirred at room temperature for 2 hours and then stirred at 60° C. for 16 hours. Methanol (40 mL) was added to this reaction solution, which was stirred at 60° C. for 1 hour and then blended with water (200 mL). The precipitated crystals were filtered and washed with water and hexane. The crystals were vacuum-dried at 60° C. for 3 hours, yielding 1-[4-(4-bromo-2-fluorobenzyloxy)-3-methoxyphenyl]ethanone (52.7 g).

Next, the above-obtained compound (52.0 g) was dissolved in THF (170 mL), and trimethylphenylammonium tribromide (57.2 g, 0.15 mol) was added thereto under ice-cooled conditions. The mixture was stirred under ice-cooled conditions for 1 hour and further stirred at room temperature for 14 hours. Water (200 mL) was added to this solution, and precipitated crystals were filtered and washed with methanol, yielding the desired compounds (59.7 g). Table 1 below shows the structure and melting point of the obtained compound.

Reference Examples 2 to 7

Each of the compounds listed in Table 1 was produced in the same manner as in Reference Example 1.

TABLE 1

| Reference Example No. | Structure | Melting Point (° C.) |
|---|---|---|
| 1 | [structure: 4-bromo-2-fluorobenzyl ether of 3-methoxy-4-hydroxyphenyl with α-bromoketone] | 139-141 |
| 2 | [structure: benzyl ether of 3-methoxy-4-hydroxyphenyl with α-bromoketone] | 101-103 |
| 3 | [structure: 4-chlorobenzyl ether] | 112-114 |
| 4 | [structure: 4-cyanobenzyl ether] | 109-111 |
| 5 | [structure: 2-cyanobenzyl ether] | 127-129 |
| 6 | [structure: 3-cyanobenzyl ether] | 122-124 |
| 7 | [structure: benzyl ether with α-bromo, α-methyl ketone] | 86-87 |

Reference Example 8

Production of 2-bromo-1-[4-(4-bromo-2-fluorobenzyloxy)-2-methoxyphenyl]ethanone 1-(2,4-dihydroxyphenyl)ethanone (25.3 g, 0.17 mol) and 4-bromo-1-bromomethyl-2-fluorobenzene (44.6 g, 0.17 mol) were dissolved in DMF (150 mL). Potassium carbonate (11.8 g, 0.09 mol) was added to the solution under ice-cooled conditions, and the mixture was stirred under ice-cooled conditions and further stirred at room temperature for 12 hours. Again, potassium carbonate (11.8 g, 0.09 mol) was added to the mixture under ice-cooled conditions, and the mixture was stirred under ice-cooled conditions for 30 minutes and further stirred at room temperature for 12 hours. Methanol (100 mL) was added to this reaction solution, and the mixture was stirred at 80° C. for 1 hour. Thereafter, water (150 mL) was added to the mixture, and precipitated crystals were filtered and washed with methanol. The crystals were vacuum-dried at 60° C. for 2 hours, yielding 1-[4-(4-bromo-2-fluorobenzyloxy)-2-hydroxyphenyl]ethanone (43.5 g, yield: 75%).

Next, the above-obtained compound (43.5 g, 0.13 mol) and potassium carbonate (21.6 g, 0.16 mol) were added to DMF (100 mL), iodomethane (27.3 g, 0.19 mol) was added dropwise to the mixture under ice-cooled conditions, and the mixture was stirred under ice-cooled conditions for 1 hour and then stirred at room temperature for 48 hours. Methanol (100 mL) was added to this reaction solution, and the mixture was stirred at 80° C. for 2 hour. Thereafter, water (150 mL) was added to the mixture, and the precipitated crystals were filtered and washed with methanol. The crystals were vacuum-dried at 60° C. for 1 hour, giving 1-[4-(4-bromo-2-fluorobenzyloxy)-2-methoxyphenyl]ethanone (42.1 g, yield: 92%).

The obtained compound (42.0 g) was dissolved in THF (100 mL), and trimethylphenylammonium tribromide (44.7 g, 0.12 mol) was added to the mixture under ice-cooled conditions. The mixture was stirred for 1 hour under ice-cooled conditions and further stirred at room temperature for 13 hours. Water (100 mL) and methanol (100 mL) were added to this solution, and the precipitated crystals were filtered and recrystallized from ethyl acetate (100 mL) and methanol (200 mL), yielding the desired compound (46.8 g). Table 2 below shows the structure and melting point of the obtained compound.

Reference Examples 9 to 12

Each of the compounds listed in Table 2 was produced in the same manner as in Reference Example 8.

TABLE 2

| Reference Example No. | Structure | Melting Point (° C.) |
|---|---|---|
| 8 | 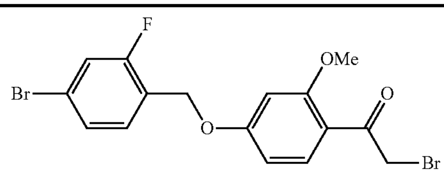 | 122-123 |
| 9 | 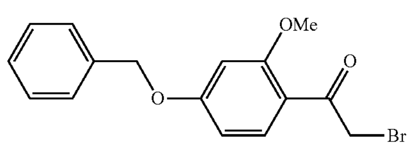 | 94-96 |
| 10 | 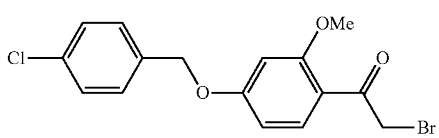 | 113-115 |
| 11 | 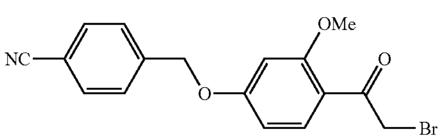 | 167-170 |
| 12 | 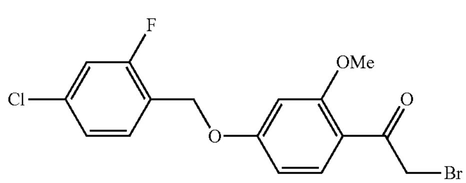 | 121-124 |

Reference Examples 13 to 27

Each of the compounds listed in Table 3 was produced in the same manner as in Reference Example 1 or 8, using the appropriate starting materials. Table 3 shows the structures of the obtained compounds.

TABLE 3

| Reference Example No. | Structure | Melting Point (° C.) |
|---|---|---|
| 13 | 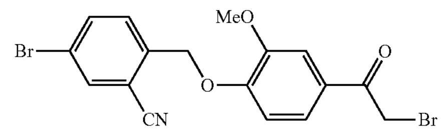 | — |
| 14 | 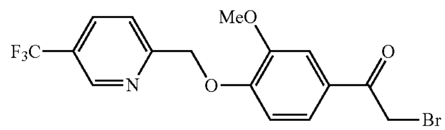 | — |
| 15 | 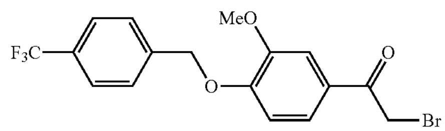 | 102-104 |
| 16 | 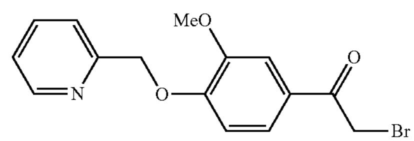 | 203-206 |
| 17 | 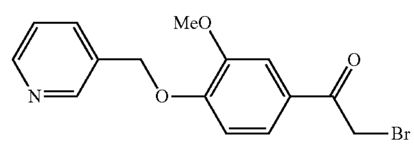 | — |
| 18 | 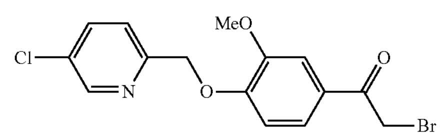 | — |
| 19 | 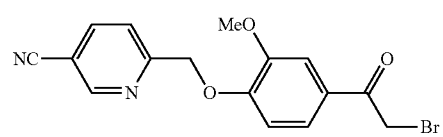 | — |
| 20 | 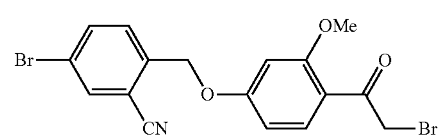 | — |
| 21 | 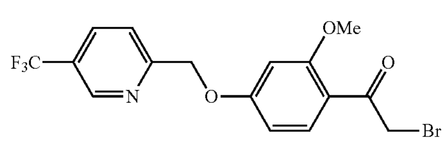 | — |

TABLE 3-continued

| Reference Example No. | Structure | Melting Point (°C.) |
|---|---|---|
| 22 | F3C—⟨phenyl⟩—O—CH2—⟨phenyl, OMe⟩—C(O)—CH2Br | 125-128 |
| 23 | ⟨2-pyridyl⟩—CH2—O—⟨phenyl, OMe⟩—C(O)—CH2Br | — |
| 24 | ⟨3-pyridyl⟩—CH2—O—⟨phenyl, OMe⟩—C(O)—CH2Br | — |
| 25 | NC—⟨pyridyl⟩—CH2—O—⟨phenyl, OMe⟩—C(O)—CH2Br | — |
| 26 | Cl—⟨pyridyl⟩—CH2—O—⟨phenyl, OMe⟩—C(O)—CH2Br | — |
| 27 | F3C—⟨pyridyl⟩—CH2—O—⟨phenyl, MeO⟩—C(O)—CH2Br | 138-142 |

Example 1

Production of 4-[4-(4-bromo-2-fluorobenzyloxy)-3-methoxyphenyl]-2-[4-(trifluoromethyl)phenyl]-1H-imidazole hydrochloride Potassium hydrogen carbonate (2.8 g, 28.0 mmol), the compound (3.0 g, 6.9 mmol) of Reference Example 1, and p-trifluoromethylbenzamidine hydrochloride dihydrate (1.6 g, 6.9 mmol) were added to a mixture solution of water (4 ml) and THF (12 ml), and the mixture solution was stirred at 60° C. for 16 hours. The reaction solution was cooled to room temperature, ethyl acetate (70 ml) was added to the solution, and the solution was stirred for 30 minutes. This solution was sequentially washed with water and saturated saline, and dried with anhydrous magnesium sulfate. After the solvent was distilled away under reduced pressure, diethyl ether was added, and the precipitated crystals were filtered. The crystals were vacuum-dried at 70° C. for 1 hour, yielding the desired compound (3.0 g). Table 4 shows the structure and properties of the obtained compound.

Examples 2 to 101

The compound of the present invention was produced in the same manner as in Example 1, using the compounds of Reference Examples 1 to 12, known 2-bromo-1-(4-hydroxy-3-methoxyphenyl)ethanone or the like, as raw materials. Table 4 shows the structures and properties of the obtained compounds.

TABLE 4

| Example No. | Structural Formula | Melting Point (°C.) | ¹H-NMR (Unless otherwise noted, DMSo-d6 solvent was used) |
|---|---|---|---|
| 1 | Br—⟨phenyl, F⟩—CH2—O—⟨phenyl, MeO⟩—⟨imidazole, NH⟩—⟨phenyl⟩—CF3 | 174-175 | 9.91 (1H, bs), 7.97 (2H, d J = 7.9), 7.65 (2H, d, J = 7.9), 7.22-7.50 (6H, m), 6.91 (1H, d, J = 8.3), 5.16 (2H, s), 3.94 (3H, s) |
| 2 | Cl—⟨phenyl⟩—CH2—O—⟨phenyl, MeO⟩—⟨imidazole, NH⟩—⟨phenyl⟩ | 87-89 | (CDCl3) 7.85-7.88 (2H, m), 7.18-7.42 (10H, m), 6.86 (1H, d, J = 8.2 Hz), 5.11 (2H, s), 3.92 (3H, s) |
| 3 | Br—⟨phenyl, F⟩—CH2—O—⟨phenyl, MeO⟩—⟨imidazole, NH, HCl⟩—⟨phenyl⟩ | 224-226 | 8.30-8.33 (2H, m), 8.24 (1H, s), 7.75 (1H, d, J = 1.7 Hz), 7.47-7.66 (7H, m), 7.23 (1H, d, J = 8.7 Hz), 5.17 (2H, s), 3.90 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 4 | | 228-229 | 8.34-8.38 (2H, m), 8.23 (1H, s), 7.72-7.76 (3H, m), 7.57 (1H, dd, J = 2.1, 8.3 Hz), 7.32-7.48 (5H, m), 7.18 (1H, d, J = 8.3 Hz), 5.16 (2H, s), 3.92 (3H, s) |
| 5 | | 244-245 | 8.18-8.20 (3H, m), 7.71 (1H, d, J = 2.1 Hz), 7.55 (1H, dd, J = 2.1, 8.3 Hz), 7.45-7.37 (7H, m), 7.19 (1H, d, J = 8.3 Hz), 5.16 (2H, s), 3.90 (3H, s), 2.42 (3H, s) |
| 6 | | 138-139 | (CDCl3) 7.83 (2H, bd, J = 8.7 Hz), 7.73 (2H, bd, J = 8.7 Hz), 7.44-7.46 (3H, m), 7.27-7.38 (3H, m), 7.22 (1H, dd, J = 2.1, 8.3 Hz), 7.21 (1H, s), 6.90 (1H, d, J = 8.3 Hz), 5.18 (2H, s), 3.97 (3H, s), 3.79 (3H, s) |
| 7 | | 229-230 | 8.17-8.20 (2H, m), 7.90 (1H, d, J = 8.7 Hz), 7.87 (1H, bs), 7.64-7.65 (3H, m), 7.33-7.50 (5H, m), 6.86 (1H, bs), 6.81 (1H, dd, J = 2.5, 8.7 Hz), 5.21 (2H, s), 3.93 (3H, s) |
| 8 | | 146-147 | 7.72-7.75 (2H, m), 7.67 (1H, s), 7.38-7.53 (8H, m), 7.31-7.35 (1H, m), 7.29 (1H, dd, J = 2.1, 8.3 Hz), 7.03 (1H, d, J = 8.3 Hz), 5.08 (2H, s), 3.83 (3H, s), 3.76 (3H, s) |
| 9 | | 146-147 | (CDCl3) 7.83 (2H, d, J = 8.3 Hz), 7.74 (2H, d, J = 8.3 Hz), 7.30-7.48 (5H, m), 7.18 (1H, s), 6.96-6.99 (2H, m), 6.92 (1H, dd, J = 2.1, 8.3 Hz), 5.22 (2H, s), 3.95 (3H, s), 3.68 (3H, s) |
| 10 | | 244-246 | 8.21-8.24 (2H, m), 7.94 (1H, d, J = 8.3), 7.87 (1H, s), 7.63-7.67 (3H, m), 7.46-7.53 (4H, m), 6.86 (1H, d, J = 2.5 Hz), 6.80 (1H, dd, J = 2.5, 8.3 Hz), 5.22 (2H, s), 3.93 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 11 | | 239-240 | 8.19-8.22 (2H, m), 7.94 (1H, d, J = 8.3 Hz), 7.88 (1H, s), 7.62-7.66 (4H, m), 7.58 (1H, t, J = 7.9 Hz), 7.49 (1H, dd, J = 1.7, 7.9 Hz), 6.87 (1H, d, J = 2.1 Hz), 6.84 (1H, dd, J = 2.1, 8.3 Hz), 5.23 (2H, s), 3.94 (3H, s) |
| 12 | | 99-103 | 8.09 (1H, d, J = 8.3 Hz), 7.98-8.04 (2H, m), 7.88 (2H, d, J = 8.3 Hz), 7.68 (2H, d, J = 8.3 Hz), 7.32-7.52 (4H, m), 6.68-6.79 (2H, m), 5.26 (2H, s), 3.91 (3H, s) |
| 13 | | 231-232 | 8.43 (2H, d, J = 8.3 Hz), 8.03 (2H, d, J = 8.3 Hz), 7.96 (1H, d, J = 8.7 Hz), 7.92 (1H, s), 7.33-7.50 (5H, m), 6.85 (1H, d, J = 2.1 Hz), 6.81 (1H, dd, J = 2.1, 8.7 Hz), 5.21 (2H, s), 3.94 (3H, s) |
| 14 | | 178-181 | 12.59 (1H, brs), 7.64 (1H, d, J = 1.6), 7.51-7.54 (2H, m), 7.45-7.47 (2H, m), 7.38-7.42 (3H, m), 7.30-7.35 (2H, m), 7.12 (1H, dd, J = 4.0, 5.2), 7.03 (1H, d, J = 8.4), 5.08 (2H, s), 3.84 (3H, s) |
| 15 | | 250-251 | 8.35 (2H, d, J = 1.6), 8.19 (1H, s), 7.86 (1H, dd, J = 1.6, 1.6), 7.63 (1H, d, J = 1.6), 7.51 (1H, dd, J = 1.6, 8.4), 7.46-7.48 (2H, m), 7.39-7.43 (2H, m), 7.34-7.36 (1H, m), 7.19 (1H, d, J = 8.4), 5.16 (2H, s), 3.89 (3H, s) |
| 16 | | 236-237 | 8.20 (1H, s), 8.19 (1H, dd, J = 2.0, 10.8), 8.05 (1H, dd, J = 2.0, 8.4), 7.71 (1H, d, J = 2.0), 7.56 (1H, dd, J = 7.6, 8.4), 7.54 (1H, dd, J = 2.0, 8.4), 7.45-7.48 (2H, m), 7.41 (2H, dd, J = 6.4, 8.4), 7.32-7.37 (1H, m), 7.18 (1H, d, J = 8.4), 5.16 (2H, s), 3.90 (3H, s), 2.34 (3H, s) |
| 17 | | 182-184 | 12.75 (1H, brs), 8.21 (2H, d, J = 8.3 Hz), 8.07 (1H, brs), 7.87 (2H, d, J = 8.3 Hz), 7.82 (2H, d, J = 8.3 Hz), 7.67 (2H, d, J = 8.3 Hz), 7.56 (1H, brs), 6.75 (1H, s), 6.71 (1H, dd, J = 2.3, 8.5 Hz), 5.26 (2H, s), 3.90 (3H, s) |

TABLE 4-continued

| Example No. | Structural Formula | Melting Point (° C.) | $^1$H-NMR (Unless otherwise noted, DMSo-d6 solvent was used) |
|---|---|---|---|
| 18 | (4-bromo-2-fluorobenzyl)oxy-2-methoxyphenyl imidazole with 4-(trifluoromethyl)phenyl | 167-170 | 12.74 (1H, brs), 8.22 (2H, d, J = 8.3 Hz), 8.05 (1H, brs), 7.83 (2H, d, J = 8.3 Hz), 7.63 (1H, dd, J = 1.9, 9.7 Hz), 7.53-7.60 (2H, m), 7.49 (1H, dd, J = 1.7, 8.3 Hz), 6.72-6.75 (2H, m), 5.17 (2H, s), 3.92 (3H, s) |
| 19 | (4-chlorobenzyl)oxy-2-methoxyphenyl imidazole with 4-(trifluoromethyl)phenyl | 158-162 | 12.70 (1H, brs), 8.20 (2H, d, J = 7.5 Hz), 8.09 (1H, d, J = 7.9 Hz), 7.82 (2H, d, J = 7.9 Hz), 7.44-7.59 (5H, m), 6.69-6.72 (2H, m), 5.14 (2H, s), 3.90 (3H, s) |
| 20 | benzyloxy-2-methoxyphenyl imidazole with thiophen-2-yl, HCl | 139-142 | 8.18 (1H, dd, J = 1.2, 3.8 Hz), 7.98 (1H, dd, J = 1.2, 5.0 Hz), 7.90 (1H, d, J = 8.8 Hz), 7.79 (1H, s), 7.48-7.51 (2H, m), 7.40-7.44 (2H, m), 7.32-7.38 (2H, m), 6.84 (1H, d, J = 2.0 Hz), 6.80 (1H, dd, J = 2.3, 8.8 Hz), 5.20 (2H, s), 3.93 (3H, s) |
| 21 | (4-cyanobenzyl)oxy-2-methoxyphenyl imidazole with thiophen-2-yl | 193-196 | 7.99 (1H, brs), 7.88 (2H, dd, J = 1.8, 6.7 Hz), 7.68 (2H, d, J = 8.5 Hz), 7.49-7.56 (3H, m), 7.13 (1H, dd, J = 3.8, 5.0 Hz), 6.69-6.74 (2H, m), 5.26 (2H, s), 3.90 (3H, s) |
| 22 | (4-chlorobenzyl)oxy-2-methoxyphenyl imidazole with thiophen-2-yl | 107-109 | 7.98 (1H, brs), 7.45-7.56 (7H, m), 7.13 (1H, dd, J = 3.8, 5.0 Hz), 6.69-6.72 (2H, m), 5.14 (2H, s), 3.90 (3H, s) |
| 23 | (4-bromo-2-fluorobenzyl)oxy-2-methoxyphenyl imidazole with thiophen-2-yl, HCl | 249-253 | 8.13 (1H, d, J = 3.8 Hz), 7.98 (1H, d, J = 5.0 Hz), 7.89 (1H, d, J = 8.5 Hz), 7.80 (1H, s), 7.63 (1H, dd, J = 1.8, 9.7 Hz), 7.58 (1H, dd, J = 8.0, 8.0 Hz), 7.50 (1H, dd, J = 1.8, 8.2 Hz), 7.34 (1H, dd, J = 4.2, 4.2 Hz), 6.84 (1H, dd, J = 2.2, 6.6 Hz), 6.81(1H, d, J = 2.0 Hz), 5.22 (2H, s), 3.93 (3H, s) |
| 24 | benzyloxy-2-methoxyphenyl imidazole with thiophen-3-yl | 188-192 | 8.03 (1H, d, J = 9.7 Hz), 7.92 (1H, s), 7.58-7.71 (2H, m), 7.44-7.58 (3H, m), 7.41 (2H, dd, J = 7.5, 7.5 Hz), 7.34 (1H, d, J = 7.2 Hz), 6.65-6.78 (2H, m), 5.13 (2H, s), 3.89 (3H, s) |

TABLE 4-continued

| Example No. | Structural Formula | Melting Point (°C.) | ¹H-NMR (Unless otherwise noted, DMSo-d6 solvent was used) |
|---|---|---|---|
| 25 | 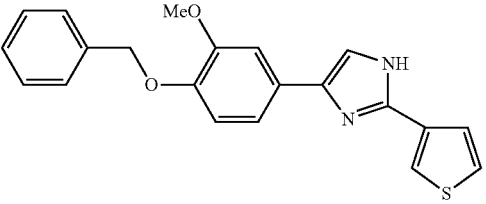 | 132-135 | 7.91 (1H, brs), 7.56-7.69 (3H, m), 7.46 (2H, d, J = 7.0 Hz), 7.40 (3H, dd, J = 7.5, 7.5 Hz), 7.34 (2H, d, J = 7.3 Hz), 7.04 (1H, d, J = 6.7 Hz), 5.09 (2H, s), 3.85 (3H, s) |
| 26 | 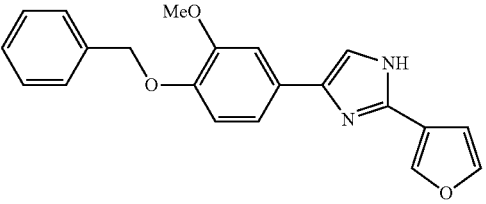 | 177-179 | 12.34 (1H, brs), 8.14 (1H, s), 7.75 (1H, s), 7.59 (1H, s), 7.33-7.47 (7H, m), 7.02 (1H, d, J = 6.6 Hz), 6.95 (1H, s), 5.08 (2H, s), 3.84 (3H, s) |
| 27 | 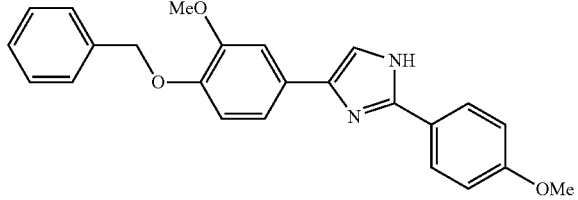 | 146-148 | 12.38 (1H, brs), 7.84-8.02 (2H, m), 7.61 (1H, s), 7.28-7.47 (7H, m), 7.03 (1H, d, J = 7.9 Hz), 5.08 (2H, s), 3.85 (3H, s), 3.80 (3H, s) |
| 28 | 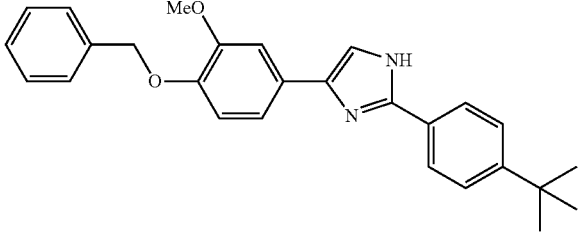 | 138-141 | 12.49 (1H, brs), 7.84-8.02 (2H, m), 7.64 (1H, s), 7.24-7.55 (9H, m), 7.03 (1H, d, J = 7.9 Hz), 5.09 (2H, s), 3.85 (3H, s), 1.31 (9H, s) |
| 29 | 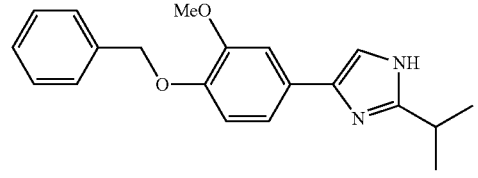 | 148-152 | 11.67 (1H, brs), 7.42-7.48 (2H, m), 7.39 (2H, dd, J = 7.5, 7.5 Hz), 7.29-7.36 (2H, m), 7.23 (1H, d, J = 7.9 Hz), 7.01-7.15 (1H, m), 6.97 (1H, d, J = 8.7 Hz), 5.06 (2H, s), 3.81 (3H, s), 2.94-3.01 (1H, m), 1.26 (6H, d, J = 7.1 Hz) |
| 30 | 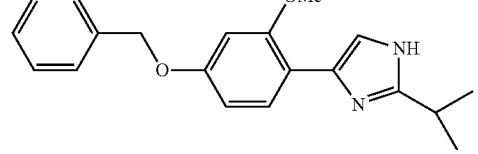 | 154-156 | 11.57 (1H, brs), 7.94 (1H, d, J = 8.7 Hz), 7.47 (2H, d, J = 7.5 Hz), 7.39 (2H, dd, J = 7.5, 7.5 Hz), 7.33 (1H, dd, J = 7.1, 7.1 Hz), 7.26 (1H, s), 6.58-6.76 (2H, m), 5.10 (2H, s), 3.85 (3H, s), 2.90-3.05 (1H, m), 1.26 (6H, d, J = 7.1 Hz) |
| 31 | 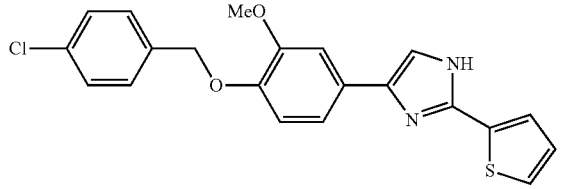 | 197-200 | 12.56 (1H, brs), 7.64 (1H, brs), 7.43-7.60 (6H, m), 7.39 (1H, brs), 7.31 (1H, d, J = 7.1 Hz), 7.13 (1H, dd, J = 4.4, 4.4 Hz), 6.97-7.09 (1H, m), 5.09 (2H, s), 3.85 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 32 | | 158-159 | (CDCl₃) 9.88 (1H, brs), 7.96 (2H, d, J = 7.9 Hz), 7.65 (2H, d, J = 8.3 Hz), 7.48 (1H, brs), 7.28-7.39 (5H, m), 7.25 (1H, s), 6.88 (1H, d, J = 8.7 Hz), 5.12 (2H, s), 3.94 (3H, s) |
| 33 | | 142-145 | 12.79 (1H, brs), 8.03 (2H, d, J = 1.2 Hz), 7.58 (1H, dd, J = 1.9, 1.9 Hz), 7.42-7.54 (6H, m), 7.36 (1H, d, J = 8.3 Hz), 7.05 (1H, d, J = 7.5 Hz), 5.11 (2H, s), 3.86 (3H, s) |
| 34 | | 160-165 | 12.61 (1H, brs), 8.16 (2H, d, J = 7.1 Hz), 7.80 (2H, d, J = 8.3 Hz), 7.47 (2H, d, J = 7.5 Hz), 7.40 (2H, dd, J = 7.5, 7.5 Hz), 7.29-7.37 (2H, m), 7.04-7.20 (2H, m), 5.11 (2H, s), 3.85 (3H, s), 2.48-2.50 (3H, s) |
| 35 | | 126-128 | 11.69 (1H, brs), 6.85-7.71 (8H, m), 5.04 (2H, s), 3.79 (3H, s), 2.90-3.05 (1H, m), 1.24 (6H, d, J = 6.6 Hz), |
| 36 | | 214-216 | 15.10 (1H, brs), 8.35-8.44 (2H, m), 8.20 (1H, s), 7.73 (1H, s), 7.50-7.60 (3H, m), 7.44-7.50 (2H, m), 7.41 (2H, dd, J = 7.3, 7.3 Hz), 7.36 (1H, d, J = 7.5 Hz), 7.19 (1H, d, J = 8.3 Hz), 5.16 (2H, s), 3.90 (3H, s) |
| 37 | | 211-213 | 8.43 (2H, d, J = 8.3 Hz), 8.24 (1H, s), 8.16 (2H, d, J = 8.7 Hz), 7.72 (1H, d, J = 1.7 Hz), 7.56 (1H, dd, J = 2.1, 8.3 Hz), 7.47 (2H, d, J = 7.1Hz), 7.40 (2H, dd, J = 7.3, 7.3 Hz), 7.35 (1H, d, J = 7.1 Hz), 7.18 (1H, d, J = 8.3 Hz), 5.16 (2H, s), 4.37(2H, q, J = 7.1 Hz), 3.90 (3H, s), 1.36 (3H, t, J = 7.1 Hz) |
| 38 | | 222-227 | 8.45 (1H, d, J = 2.5 Hz), 8.43(1H, d, J = 2.5 Hz), 8.24 (1H, s), 8.16 (2H, dd, J = 1.9, 8.5 Hz), 7.73 (1H, dd, J = 2.7, 2.7 Hz), 7.53-7.59 (1H, m), 7.46-7.48 (2H, m), 7.39-7.43 (2H, m), 7.31-7.37 (1H, m), 7.18 (1H, d, J = 8.3 Hz), 5.16 (2H, s), 3.91 (3H, s), 3.91 (3H, s) |

TABLE 4-continued

| Example No. | Structural Formula | Melting Point (°C.) | ¹H-NMR (Unless otherwise noted, DMSo-d6 solvent was used) |
|---|---|---|---|
| 39 | (structure: benzyloxy-methoxyphenyl-imidazole-benzoic acid, HCl) | 241-243 | 8.42 (2H, d, J = 8.3 Hz), 8.25 (1H, s), 8.15 (2H, d, J = 8.3 Hz), 7.73 (1H, d, J = 1.7 Hz), 7.57 (1H, dd, J = 1.9, 8.5 Hz), 7.47 (2H, d, J = 7.1 Hz), 7.41 (2H, dd, J = 7.5, 7.5 Hz), 7.35 (1H, d, J = 7.5 Hz), 7.18 (1H, d, J = 8.7 Hz), 5.16 (2H, s), 3.91 (3H, s) |
| 40 | (structure: benzyloxy-methoxyphenyl-2-methylimidazole) | 159-163 | 11.69 (1H, brs), 7.44 (2H, d, J = 7.5 Hz), 7.38 (2H, dd, J = 7.3, 7.3 Hz), 7.32 (3H, dd, J = 7.1, 7.1 Hz), 7.10-7.21 (2H, m), 6.98 (2H, d, J = 7.9 Hz) 5.06 (2H, s), 3.81 (3H, s), 2.29 (3H, s) |
| 41 | (structure: hydroxy-methoxyphenyl-imidazole-trifluoromethylphenyl) | 197-198 | 14.40 (1H, brs), 9.54 (1H, brs), 8.31 (2H, d, J = 8.3 Hz), 8.21 (1H, s), 8.08 (2H, d, J = 8.3 Hz), 7.49 (1H, d, J = 1.7 Hz), 7.36 (1H, dd, J = 1.9, 8.1 Hz), 6.93 (1H, d, J = 8.3 Hz), 3.89 (3H, s) |
| 42 | (structure: benzyloxy-methoxyphenyl-imidazole-fluorophenyl, HCl) | 217-220 | 8.18 (2H, dd, J = 5.0, 9.1 Hz), 7.82-7.84 (2H, m), 7.44-7.54 (4H, m), 7.40 (2H, dd, J = 7.3, 7.3 Hz), 7.30-7.36 (1H, m), 6.82 (1H, d, J = 2.1 Hz), 6.78 (1H, dd, J = 2.1, 87 Hz), 5.18 (2H, s), 3.90 (3H, s) |
| 43 | (structure: chlorobenzyloxy-methoxyphenyl-imidazole-fluorophenyl) | 174-176 | 12.49 (1H, brs), 8.01-8.06 (3H, m), 7.43-7.50 (5H, m), 7.28 (2H, dd, J = 8.7, 8.7 Hz), 6.62-6.78 (2H, m), 5.11 (2H, s), 3.87 (3H, s) |
| 44 | (structure: hydroxy-methoxyphenyl-imidazole-fluorophenyl) | 116-123 | (CDCl₃) 11.70 (1H, brs), 7.96-8.03 (2H, m), 7.33 (1H, s), 7.24 (1H, s), 7.21 (1H, d, J = 7.9 Hz), 7.04-7.13 (2H, m), 6.90 (1H, d, J = 8.3 Hz), 3.94 (3H, s) |
| 45 | (structure: cyanobenzyloxy-methoxyphenyl-imidazole-fluorophenyl, HCl) | 189-191 | 12.49 (1H, brs), 8.04-8.10 (3H, m), 7.89 (2H, d, J = 8.3Hz), 7.68 (2H, d, J = 7.9 Hz), 7.52 (1H, s), 7.31 (2H, dd, J = 8.9, 8.9 Hz), 6.75 (1H, s), 6.70 (1H, d, J = 7.9 Hz), 5.26 (2H, s), 3.91 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 46 | | 212-215 | 14.90 (1H, brs), 8.26 (1H, d, J = 10.4 Hz), 8.22 (1H, s), 8.15 (1H, d, J = 7.9 Hz), 7.67-7.73 (2H, m), 7.56 (1H, dd, J = 1.9, 8.5 Hz), 7.46-7.51 (3H, m), 7.41 (2H, dd, J = 7.5, 7.5 Hz), 7.31-7.37 (1H, m), 7.19 (1H, d, J = 8.3 Hz), 5.16 (2H, s), 3.90 (3H, s) |
| 47 | | 226-227 | 14.95 (1H, brs), 8.54 (1H, dd, J = 8.9, 8.9 Hz), 8.15-8.25 (2H, m), 7.77 (1H, dd, J = 9.1, 9.1 Hz), 7.70-7.73 (1H, m), 7.54 (1H, d, J = 8.3 Hz), 7.46 (2H, d, J = 7.5 Hz), 7.40 (2H, dd, J = 7.5, 7.5 Hz), 7.34 (1H, dd, J = 7.1, 7.1 Hz), 7.18 (1H, d, J = 8.7 Hz), 5.15 (2H, s), 3.90 (3H, s) |
| 48 | | 243-245 | 15.01 (1H, brs), 8.36 (2H, dd, J = 5.2, 8.9 Hz), 8.20 (1H, s), 7.71 (1H, d, J = 2.1 Hz), 7.46-7.56 (7H, m), 7.18 (1H, d, J = 8.3 Hz), 5.17 (2H, s), 3.90 (3H, s) |
| 49 | | 214-218 | 12.31 (1H, brs), 7.93-8.04 (2H, m), 7.46 (2H, d, J = 7.1 Hz), 7.39 (2H, dd, J = 7.3, 7.3 Hz), 7.23-7.36 (4H, m), 7.00-7.20 (2H, m), 5.09 (2H, s), 3.83 (3H, s) 2.43 (3H, s) |
| 50 | | 204-206 | (CDCl₃) 11.87 (1H, brs), 8.02 (2H, dd, J = 5.2, 8.5 Hz), 7.75 (1H, d, J = 7.9 Hz), 7.69 (1H, d, J = 7.9 Hz), 7.63 (1H, dd, J = 7.7, 7.7 Hz), 7.43 (2H, dd, J = 7.7, 7.7 Hz), 7.23-7.31 (2H, m), 7.10 (2H, dd, J = 8.7, 8.7 Hz), 6.95 (1H, d, J = 8.3 Hz), 5.34 (2H, s), 3.98 (3H, s) |
| 51 | | 173-174 | 12.86 (1H, s), 8.21 (2H d, J = 8.3 Hz), 7.84 (2H, d, J = 8.3 Hz), 7.76 (1H, brs), 7.62 (1H, dd, J = 1.9, 9.7 Hz), 7.47-7.55 (3H, m), 7.39 (1H, d, J = 7.9 Hz), 7.09 (1H, d, J = 7.9 Hz), 5.12 (2H, s), 3.85 (3H, s) |
| 52 | | 228-233 | 8.29-8.36 (2H, m), 8.19 (1H, s), 7.68 (1H, d, J = 2.1 Hz), 7.62 (1H, dd, J = 1.9, 9.7 Hz), 7.46-7.55 (5H, m), 7.21 (1H, d, J = 8.7 Hz), 5.15 (2H, s), 3.87 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 53 | | 244-247 | 8.16-8.20 (2H, m), 8.09 (1H, d, J = 7.9 Hz), 7.67-7.72 (2H, m), 7.62 (1H, dd, J = 1.7, 10.0 Hz), 7.46-7.55 (4H, m), 7.22 (1H, d, J = 8.7 Hz), 5.16 (2H, s), 3.87 (3H, s) |
| 54 | | 231-235 | 8.18 (1H, d, J = 10.0 Hz), 8.09 (1H, d, J = 8.3 Hz), 7.96 (1H, d, J = 8.7 Hz), 7.88 (1H, s), 7.65-7.74 (1H, m), 7.45-7.52 (3H, m), 7.38-7.45 (2H, m), 7.32-7.38 (2H, m), 6.85 (1H, d, J = 2.5 Hz), 6.81(1H, dd, J = 2.5, 8.7 Hz), 5.21 (2H, s), 3.93 (3H, s) |
| 55 | | 231-233 | 12.87 (1H, brs], 8.21 (2H, d, J = 7.9 Hz), 7.80-7.89 (5H, m), 7.66(2H, d, J = 8.3), 7.49 (1H, brs), 7.38 (1H, d, J = 7.9 Hz), 7.05 (1H, d, J = 7.9 Hz), 5.23 (2H, s), 3.89 (3H, s) |
| 56 | | 224-226 | 12.58 (1H, brs), 7.97-8.11 (2H, m), 7.88 (2H, d, J = 8.3 Hz), 7.62-7.72 (3H, m), 7.49 (1H, s), 7.29-7.37 (3H, m), 7.02 (1H, d, J = 7.9 Hz), 5.22 (2H, s), 3.88 (3H, s) |
| 57 | | >250 | 14.44 (1H, brs) 8.21-8.25 (2H, m), 7.93 (1H, d, J = 8.3 Hz), 7.81 (1H, s), 7.63 (1H, dd, J = 1.9, 8.3 Hz), 7.57 (1H, dd, J = 7.9, 7.9 Hz), 7.45-7.53 (3H, m), 6.79-6.84 (2H, m), 5.20 (2H, s), 3.92 (3H, s) |
| 58 | | >250 | 8.64 (1H, s), 8.54 (1H, d, J = 7.9 Hz), 7.98 (2H, dd, J = 8.1, 8.1 Hz), 7.91 (1H, s), 7.87 (1H, dd, J = 7.9, 7.9 Hz), 7.63 (1H, dd, J = 1.7, 9.5 Hz), 7.57 (1H, dd, J = 8.1, 8.1 Hz), 7.49 (1H, dd, J = 1.9, 8.1 Hz), 6.82-6.86 (2H, m), 5.21 (2H, s), 3.93 (3H, s) |
| 59 | | 205-209 | 12.71 (1H, brs), 7.82-7.95 (3H, m), 7.71-7.82 (2H, m), 7.66 (2H, d, J = 8.7 Hz), 7.49-7.54 (2H, m), 7.31-7.41 (1H, m), 7.14-7.23 (1H, m), 7.00-7.08 (1H, m), 5.22 (2H, s), 3.88 (3H, s) |

TABLE 4-continued

| Example No. | Structural Formula | Melting Point (°C.) | ¹H-NMR (Unless otherwise noted, DMSo-d6 solvent was used) |
|---|---|---|---|
| 60 | 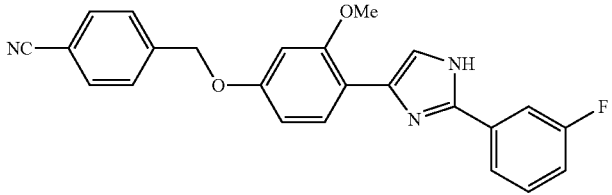 | 257-260 | 8.18 (1H, d, J = 10.0 Hz), 8.10 (1H, d, J = 7.5 Hz), 7.98 (1H, d, J = 8.7 Hz), 7.87-7.89 (3H, m), 7.64-7.71 (3H, m), 7.47 (1H, ddd, J = 2.2, 8.5, 8.5 Hz), 6.86 (1H, d, J = 2.1 Hz), 6.79 (1H, dd, J = 2.1, 8.7 Hz), 5.32 (2H, s), 3.92 (3H, s) |
| 61 | 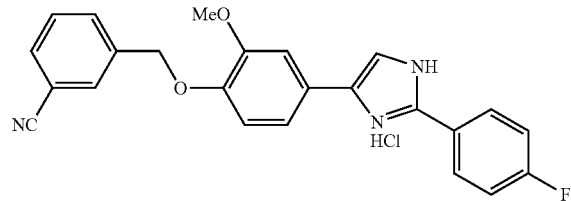 | 242-244 | 8.33-8.37 (2H, m), 8.20 (1H, s), 7.93 (1H, s), 7.81-7.84 (2H, m), 7.72 (1H, d, J = 2.1 Hz), 7.64 (1H, dd, J = 7.9, 7.9 Hz), 7.50-7.59 (3H, m), 7.20 (1H, d, J = 8.3Hz), 5.23 (2H, s), 3.92 (3H, s) |
| 62 | 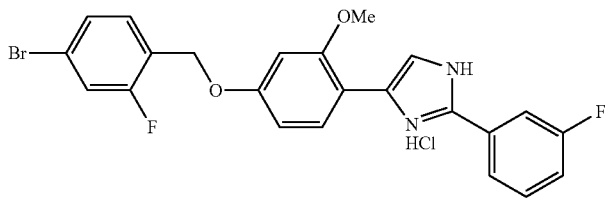 | 240-245 | 8.15 (1H, d, J = 8.7 Hz), 8.07 (1H, d, J = 6.6 Hz), 7.96 (1H, d, J = 5.8 Hz), 7.89 (1H, s), 7.55-7.72 (3H, m), 7.46-7.50 (2H, m), 6.81-6.85 (2H, m), 5.21(2H, s), 3.93 (3H, s) |
| 63 | 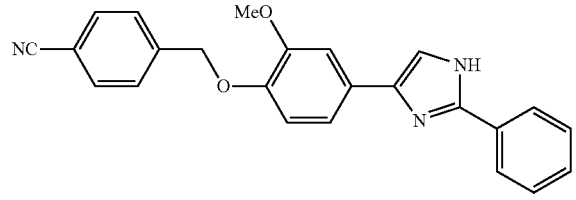 | 193-196 | 7.87 (2H, d, J = 7.1 Hz), 7.63 (2H, d, J = 8.0 Hz), 7.54 (2H, d, J = 8.0 Hz), 7.32-7.41 (3H, m), 7.28 (1H, s), 7.21 (1H, d, J = 7.9 Hz), 6.83 (1H, d, J = 8.3 Hz), 5.18 (2H, s), 3.91 (3H, s) |
| 64 | 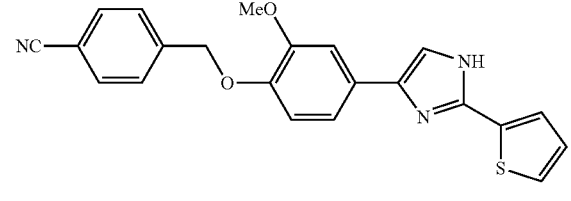 | 192-193 | 7.81 (2H, d, J = 8.7 Hz),7.65 (2H, d, J = 8.7 Hz), 7.55 (1H, dd, J = 1.0, 3.5 Hz), 7.41-7.47 (3H, m), 7.30 (1H, dd, J = 1.7, 8.3 Hz), 7.11 (1H, dd, 3.5, 3.5 Hz), 7.03 (1H, d, J = 8.3 Hz), 5.20 (1H, s), 3.88 (3H, s) |
| 65 | 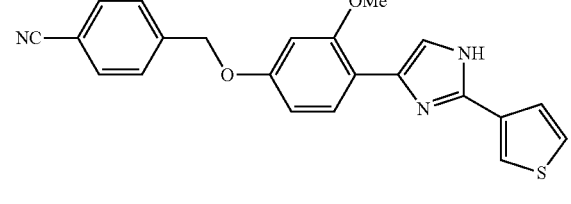 | 183-186 | 12.34 (1H, brs), 8.06 (1H, d, J = 8.3 Hz), 7.87-7.91 (3H, m), 7.61-7.73 (4H, m), 7.46 (1H, s), 6.72 (1H, d, J = 1.9 Hz), 6.69 (1H, dd, J = 1.9, 8.0 Hz), 5.27 (2H, s), 3.92 (3H, s) |
| 66 | 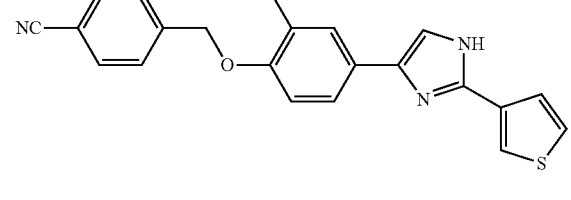 | 176-180 | 12.46 (1H, brs), 7.91 (1H, dd, J = 2.1, 2.1 Hz), 7.88, (2H, d, J = 8.3 Hz), 7.63-7.67 (5H, m), 7.46 (1H, d, J = 1.7 Hz), 7.35 (1H, dd, J = 1.9, 8.1 Hz), 7.01 (1H, d, J = 8.7 Hz), 5.21 (2H, s), 3.87 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 67 | | 177-179 | 12.55 (1H, brs), 7.60 (1H, dd, J = 1.7, 8.0 Hz), 7.45-7.56 (5H, m), 7.38 (1H, s), 7.31 (1H, d, J = 7.5 Hz), 7.12 (1H, dd, J = 3.5, 5.2 Hz), 7.05 (1H, d, J = 7.9 Hz), 5.09 (2H, s), 3.82 (3H, s) |
| 68 | | 247-249 | 8.62 (1H, d, J = 1.7 Hz), 7.97 (1H, d, J = 8.0 Hz), 7.95 (1H, dd, J = 1.7, 8.0 Hz), 7.81 (1H, dd, J = 2.9, 5.0 Hz), 7.75 (1H, s), 7.62 (1H, dd, J = 1.7, 9.5 Hz), 7.56 (1H, dd, J = 8.1, 8.1 Hz), 7.48 (1H, dd, J = 3.7, 11.1 Hz), 6.78-6.82 (2H, m), 5.09 (2H, s), 3.92 (3H, s) |
| 69 | | 251-252 | 8.83 (1H, dd, J = 1.2, 2.9 Hz), 8.14 (1H, s), 8.04 (1H, dd, J = 1.2, 5.0 Hz), 7.85 (1H, dd, J = 2.9, 5.4 Hz), 7.72 (1H, d, J = 2.1 Hz), 7.61 (1H, dd, J = 1.9, 9.7 Hz), 7.46-7.55 (3H, m), 7.20 (1H, d, J = 8.3 Hz), 5.15 (2H, s), 3.88 (3H, s) |
| 70 | | 238-241 | 8.68 (1H, dd, J = 1.2, 2.9 Hz), 7.95 (1H, dd, J = 1.2, 5.0 Hz), 7.92 (1H, d, J = 8.7 Hz), 7.84 (1H, dd, J = 2.9, 5.0 Hz), 7.79 (1H, s), 7.51 (2H, d, J = 8.0 Hz), 7.46 (2H, d, J = 8.0 Hz), 6.82 (1H, d, J = 2.1 Hz), 6.78 (1H, dd, J = 2.3, 8.5 Hz), 5.19 (2H, s), 3.91 (3, s) |
| 71 | | 197-201 | 12.42 (1H, brs), 7.91 (1H, s), 7.30-7.63 (9H, m), 7.01 (1H, d, J = 7.9 Hz), 5.08 (2H, s), 3.84 (3H, s) |
| 72 | | 224-227 | 8.78 (1H, d, J = 1.7 Hz), 8.09 (1H, s), 8.01 (1H, dd, J = 1.2, 5.0 Hz), 7.90 (1H, s), 7.79-7.84 (3H, m), 7.70 (1H, d, J = 1.7 Hz), 7.62 (1H, dd, J = 7.7, 7.7 Hz), 7.52 (1H, dd, J = 2.1, 8.3 Hz), 7.16 (1H, d, J = 8.7 Hz), 5.20 (2H, s), 3.90 (3H, s) |
| 73 | | 236-237 | 8.78 (1H, dd, J = 1.2, 2.9 Hz), 8.14 (1H, s), 8.00 (1H, dd, J = 1.2, 5.0 Hz), 7.91 (1H, d, J = 7.9 Hz), 7.85 (1H, dd, J = 2.9, 5.0 Hz), 7.69-7.78 (3H, m), 7.52-7.60 (2H, m), 7.23 (1H, d, J = 8.7 Hz), 5.27 (2H, s), 3.88 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 74 | NC-C₆H₄-CH₂-O-C₆H₃(OMe)-[imidazole-NH]-C₆H₄-CF₃ · HCl | 248-250 | 8.56 (1H, s), 8.45 (1H, d, J = 7.9 Hz), 7.96 (1H, d, J = 7.9 Hz), 7.84-7.90 (5H, m), 7.67 (2H, d, J = 7.9 Hz), 6.85 (1H, s), 6.79 (1H, d, J = 8.3 Hz), 5.31 (2H, s), 3.92 (3H, s) |
| 75 | NC-C₆H₄-CH₂-O-C₆H₃(MeO)-[imidazole-NH]-C₆H₄-CF₃ · HCl | 231-232 | 8.72 (1H, s), 8.64 (1H, d, J = 7.9 Hz), 8.24 (1H, s), 7.97 (1H, d, J = 7.9 Hz), 7.80-7.90 (3H, m), 7.74 (1H, s), 7.65 (2H, d, J = 7.9 Hz), 7.55 (1H, d, J = 7.9 Hz), 7.18 (1H, d, J = 8.7 Hz), 5.29 (2H, s), 3.93 (3H, s) |
| 76 | NC-C₆H₄-CH₂-O-C₆H₃(OMe)-[imidazole-NH]-C₆H₄-Cl | 186-187 | 12.57 (1H, brs), 8.00-8.06 (3H, m), 7.87 (2H, d, J = 7.9 Hz), 7.67 (2H, d, J = 7.9 Hz), 7.45-7.55 (2H, m), 6.74 (1H, s), 6.69 (1H, s), 5.25 (2H, s), 3.89 (3H, s) |
| 77 | NC-C₆H₄-CH₂-O-C₆H₃(MeO)-[imidazole-NH]-C₆H₄-Cl | 231-232 | 12.67 (1H, brs), 8.01 (2H, d, J = 7.9 Hz), 7.88 (2H, d, J = 8.3 Hz), 7.60-7.72 (3H, m), 7.35-7.60 (4H, m), 7.04 (1H, d, 7.5 Hz), 5.22 (2H, s), 3.88 (3H, s) |
| 78 | Cl-C₆H₄-CH₂-O-C₆H₃(OMe)-[imidazole-NH]-C₆H₄-F · HCl | 231-232 | 14.92 (1H, brs), 8.13 (1H, d, J = 7.9 Hz), 8.09 (1H, d, J = 8.0 Hz), 7.96 (1H, d, J = 8.3 Hz), 7.88 (1H, s), 7.69 (1H, d, J = 6.2 Hz), 7.40-7.60 (5H, m), 6.84 (1H, s), 6.79 (1H, d, J = 7.9 Hz), 5.20 (2H, s), 3.92 (3H, s) |
| 79 | Cl-C₆H₄-CH₂-O-C₆H₃(MeO)-[imidazole-NH]-C₆H₄-F · HCl | 235-237 | 15.11 (1H, brs), 8.20-8.30 (2H, m), 8.15 (1H, d, J = 7.1 Hz), 7.72 (2H, s), 7.55 (1H, d, J = 7.9 Hz), 7.40-7.65 (5H, m), 7.18 (1H, d, J = 8.3 Hz), 5.17 (2H, s), 3.91 (3H, s) |
| 80 | Br-C₆H₃(F)-CH₂-O-C₆H₃(OMe)-[imidazole-NH]-C₆H₄-Cl | 191-195 | 12.55 (1H, brs), 8.07 (1H, d, J = 8.0 Hz), 8.00 (2H, d, J = 8.3 Hz), 7.61 (1H, dd, J = 1.9, 9.7 Hz), 7.46-7.57 (5H, m), 6.70-6.80 (2H, m), 5.14 (2H, s), 3.89 (3H, s) |

TABLE 4-continued

| Example No. | Structural Formula | Melting Point (° C.) | $^1$H-NMR (Unless otherwise noted, DMSo-d6 solvent was used) |
|---|---|---|---|
| 81 | | 224-228 | 14.89 (1H, brs), 7.93-8.06 (5H, m), 7.80 (1H, d, J = 8.7 Hz), 7.63 (1H, dd, J = 1.9, 9.7 Hz), 7.56 (1H, dd, J = 8.1, 8.1 Hz), 7.48 (1H, dd, J = 1.9, 8.1 Hz), 6.86 (1H, d, J = 2.5 Hz), 6.81 (1H, dd, J = 2.5, 8.7 Hz), 5.20 (2H, s), 3.93 (3H, s) |
| 82 | | 181-184 | 12.51(1H, brs), 8.03 (1H, s), 8.01 (2H, d, J = 8.3 Hz), 7.44-7.52 (7H, m), 6.67-6.72 (2H, m), 5.13 (2H, s), 3.89 (3H, s) |
| 83 | | 158-161 | 12.29 (1H, brs), 7.98 (1H, brs), 7.86 (1H, d, J = 7.9 Hz), 7.70-7.78 (2H, m), 7.65 (1H, dd, J = 7.5, 7.5 Hz), 7.44-7.51 (5H, m), 6.72 (1H, s), 6.66 (1H, dd, J = 2.3, 8.5 Hz), 5.13 (2H, s), 3.89 (3H, s) |
| 84 | | 160-162 | 12.39 (1H, brs), 8.08 (1H, d, J = 7.9 Hz), 7.88 (2H, d, J = 7.5 Hz), 7.61 (1H, dd, J = 2.0, 8.0 Hz), 7.55(1H, dd, J = 8.0, 8.0 Hz), 7.46-7.48 (2H, m), 7.25 (2H, d, J = 7.9 Hz), 6.61-6.79 (2H, m), 5.14 (2H, s), 3.89 (2H, s), 2.33 (3H, s) |
| 85 | | 195-198 | 12.38 (1H, brs), 8.07 (1H, d, J = 8.3 Hz), 7.87 (4H, d, J = 8.3 Hz), 7.67 (2H, d, J = 8.3 Hz), 7.48 (1H, s), 7.26 (2H, d, J = 7.9 Hz), 6.67-6.73 (2H, m), 5.25 (2H, s), 3.89 (3H, s), 2.33 (3H, s) |
| 86 | | >250 | 8.17 (2H, d, J = 8.7 Hz), 7.93 (1H, d, J = 8.7 Hz), 7.78 (1H, s), 7.62 (1H, dd, J = 1.9, 8.7 Hz), 7.57 (1H, dd, J = 8.1, 8.1 Hz), 7.48 (1H, dd, J = 1.9, 8.1 Hz), 7.19 (2H, d, J = 8.7 Hz), 6.80-6.84 (2H, m), 5.21 (2H, s), 3.92 (3H, s), 3.86 (3H, s) |

TABLE 4-continued

| Example No. | Structural Formula | Melting Point (° C.) | $^1$H-NMR (Unless otherwise noted, DMSo-d6 solvent was used) |
|---|---|---|---|
| 87 | (4-cyanobenzyl-O-)(2-OMe)phenyl-imidazole-(4-OMe-phenyl), HCl | 183-186 | 14.57 (1H, bs), 8.21 (2H, d, J = 8.7 Hz), 7.95 (1H, d, J = 8.7 Hz), 7.88 (2H, d, J = 8.3 Hz), 7.79 (1H, s), 7.67 (2H, d, J = 8.3 Hz), 7.19 (2H, d, J = 8.7 Hz), 6.86 (1H, d, J = 2.1), 6.79 (1H, dd, J = 2.1, 8.7), 5.32 (2H, s), 3.92 (3H, s), 3.86 (3H, s) |
| 88 | (4-Br-2-F-benzyl-O-)(2-OMe)phenyl-imidazole-(3-Cl-phenyl), HCl | 231-236 | 8.35-8.36 (1H, m), 8.19 (1H, ddd, J = 2.4, 2.4, 4.5), 7.96 (1H, d, J = 8.7 Hz), 7.88 (1H, s), 7.54-7.69 (4H, m), 7.48 (1H, dd, J = 1.9, 8.1 Hz), 6.80-6.84 (2H, m), 5.21 (2H, s), 3.92 (3H, s) |
| 89 | (4-Br-2-F-benzyl-O-)(2-OMe)phenyl-imidazole-(3,4-diF-phenyl) | 263-265 | 8.36-8.44 (1H, m), 8.06-8.14 (1H, m), 7.95 (1H, d, J = 8.3Hz), 7.87 (1H, s), 7.60-7.70 (1H, m), 7.62 (1H, dd, J = 1.9, 8.0 Hz), 7.56 (1H, dd, J = 8.0, 8.0 Hz), 7.48 (1H, dd, J = 1.9, 8.1 Hz), 6.77-6.87 (2H, m), 5.20 (2H, s), 3.92 (3H, s) |
| 90 | (4-Br-2-F-benzyl-O-)(2-OMe)phenyl-imidazole-(4-t-Bu-phenyl) | 177-180 | 12.40 (1H, brs), 8.08 (1H, d, J = 8.7 Hz), 7.90 (2H, d, J = 8.3 Hz), 7.38-7.74 (6H, m), 6.63-6.81 (2H, m), 5.14 (2H, s), 3.89 (3H, s), 1.30 (9H, s) |
| 91 | (4-Br-2-F-benzyl-O-)(2-OMe)phenyl-imidazole-(3,5-diCl-phenyl) | 260-265 | 8.30 (2H, d, J = 1.7 Hz), 7.94 (1H, d, J = 8.3 Hz), 7.89 (1H, s), 7.83-7.86 (1H, m), 7.63 (1H, d, J = 1.7, 8.0 Hz), 7.57 (1H, dd, J = 8.0, 8.0 Hz), 7.48 (1H, dd, J = 1.7, 8.3 Hz), 6.78-6.88 (2H, m), 5.21 (2H, s), 3.93 (3H, s) |
| 92 | (4-Br-2-F-benzyl-O-)(2-OMe)phenyl-imidazole-(4-CO$_2$Me-phenyl) | 158-159 | 8.13 (2H, d, J = 8.3 Hz), 7.98-8.07 (3H, m), 7.61 (1H, dd, J = 1.7, 9.5 Hz), 7.51-7.58 (2H, m), 7.47 (1H, dd, J = 1.7, 8.3 Hz), 6.68-6.76 (2H, m), 5.15 (2H, s), 3.90 (3H, s), 3.86 (3H, s) |

TABLE 4-continued

| Example No. | Structural Formula | Melting Point (°C.) | ¹H-NMR (Unless otherwise noted, DMSo-d6 solvent was used) |
|---|---|---|---|
| 93 | (structure: 4-bromo-2-fluorobenzyloxy-methoxyphenyl-imidazole-3,4-dimethoxyphenyl · HCl) | 255-256 | 7.93 (1H, d, J = 8.3 Hz), 7.89 (1H, d, J = 2.1 Hz), 7.79-7.82 (2H, m), 7.62 (1H, dd, J =1.9, 8.0 Hz), 7.56 (1H, dd, J =8.0, 8.0 Hz), 7.48 (1H, dd, J = 1.9, 8.1 Hz), 7.20 (1H, d, J = 8.7 Hz), 6.84 (1H, d, J = 2.1 Hz), 6.81 (1H, dd, J = 2.3, 8.5 Hz), 5.21 (2H, s), 3.92 (3H, s), 3.89 (3H, s), 3.85 (3H, s) |
| 94 | (structure: 4-bromo-2-fluorobenzyloxy-methoxyphenyl-imidazole-4-carboxyphenyl · HCl) | >250 | 8.26 (2H, d, J = 8.3 Hz), 8.07 (2H, d, J = 8.7 Hz), 7.99 (1H, d, J = 8.3 Hz), 7.76 (1H, s), 7.58 (1H, dd, J = 1.7, 9.2 Hz), 7.54 (1H, d, J = 8.0 Hz), 7.46 (1H, dd, J = 1.7, 8.3 Hz), 6.72-6.81 (2H, m), 5.17 (2H, s), 3.90 (3H, s) |
| 95 | (structure: 4-bromo-2-fluorobenzyloxy-methoxyphenyl-imidazole-3-methylphenyl) | 120-123 | 12.44 (1H, brs), 8.07 (1H, d, J = 9.1 Hz), 7.81 (1H, s), 7.76 (1H, d, J = 7.1 Hz), 7.40-7.64 (4H, m), 7.32 (1H, dd, J = 7.7, 7.7 Hz), 7.15 (1H, d, J = 7.5 Hz), 6.70 (2H, s), 5.13 (2H, s), 3.88 (3H, s), 2.36 (3H, s) |
| 96 | (structure: 4-cyanobenzyloxy-methoxyphenyl-imidazole-3,4-difluorophenyl) | 173-176 | 12.59 (1H, brs), 7.80-8.09 (5H, m), 7.65 (2H, d, J = 8.0 Hz), 7.45-7.55 (2H, m), 6.72 (1H, s), 6.68 (1H, d, J = 7.9 Hz), 5.23 (2H, s), 3.87 (3H, s) |
| 97 | (structure: 4-cyanobenzyloxy-methoxyphenyl-imidazole-3-chlorophenyl) | 154-157 | 12.64 (1H, brs), 7.95-8.10 (2H, m), 7.93 (1H, d, J = 7.2 Hz), 7.84 (2H, d, J = 8.0 Hz), 7.65 (2H, d, J = 8.0 Hz), 7.53 (1H, s), 7.47 (1H, dd, J = 8.0, 8.0 Hz), 7.38 (1H, d, J = 7.2 Hz), 6.72 (1H, s), 6.68 (1H, d, J = 8.7 Hz), 5.23 (2H, s), 3.87 (3H, s) |
| 98 | (structure: 4-chlorobenzyloxy-methoxyphenyl-imidazole-4-methylphenyl · HCl) | 241-244 | 7.94 (2H, d, J = 7.9 Hz), 7.74-7.82 (2H, m), 7.39-7.54 (6H, m), 6.80 (1H, s), 6.76 (1H, d, J = 8.7 Hz), 5.17 (2H, s), 3.89 (3H, s), 2.39 (3H, s) |

TABLE 4-continued

| Example No. | Structural Formula | Melting Point (° C.) | ¹H-NMR (Unless otherwise noted, DMSo-d6 solvent was used) |
|---|---|---|---|
| 99 | (structure: 4-bromo-2-fluorobenzyl ether linked to 2-methoxyphenyl-imidazole-(3-methoxyphenyl), HCl salt) | 255-258 | 7.82 (1H, s), 7.80 (1H, d, J = 8.3 Hz), 7.43-7.70 (6H, m), 7.18 (2H, d, J = 8.3 Hz), 6.75-6.87 (2H, m), 5.19 (2H, s), 3.90 (3H, s), 3.85 (3H, s) |
| 100 | (structure: 4-cyanobenzyl ether linked to 2-methoxyphenyl-imidazole-(3-methoxyphenyl)) | 139-142 | 12.49 (1H, brs), 8.09 (1H, d, J = 8.0 Hz), 7.88 (2H, d, J = 8.3 Hz), 7.69 (2H, d, J = 8.3 Hz), 7.58-7.65 (2H, m), 7.52 (1H, s), 7.37 (1H, dd, J = 8.0, 8.0 Hz), 6.92 (1H, d, 2.5 Hz), 6.74 (1H, d, J = 2.5 Hz), 6.70 (1H, dd, J = 2.3, 8.5 Hz), 5.26 (2H, s), 3.91 (3H, s), 3.83 (3H, s) |
| 101 | (structure: 4-chlorobenzyl ether linked to 2-methoxyphenyl-imidazole-(3-methoxyphenyl), HCl salt) | 256-258 | 7.90 (1H, d, J = 7.9 Hz), 7.84 (1H, s), 7.80 (1H, s), 7.73(1H, d, J = 7.9 Hz), 7.46-7.59 (5H, m), 7.19 (1H, d, J = 6.2 Hz), 6.85(1H, d, 2.1 Hz), 6.80 (1H, dd, J =2.3, 8.5 Hz), 5.21 (2H, s), 3.93 (3H, s), 3.88 (3H, s) |

Examples 102 to 139

The compound of the present invention was produced in the same manner as in Example 1, using the compounds of reference examples or appropriate starting materials. Table 5 shows the structures and properties of the obtained compounds.

TABLE 5

| Example No. | Structural Formula | Melting Point (° C.) | ¹H-NMR (DMSO-$d_6$) |
|---|---|---|---|
| 102 | (structure: 4-bromo-2-fluorobenzyl ether linked to 2-methoxyphenyl-imidazole-(3,4-dichlorophenyl), HCl salt) | 260-262 | 8.63 (1 H, d, J = 1.7 Hz), 8.27 (1 H, dd, J = 1.7, 8.7 Hz), 8.04 (1 H, d, J = 8.5 Hz), 7.92 (1 H, d, J = 8.7 Hz), 7.87 (1 H, s), 7.64 (1 H, dd, J = 1.7, 8.7 Hz), 7.58 (1 H, dd, J = 8.7, 8.7 Hz), 7.50 (1 H, dd, J = 1.7, 8.7 Hz), 6.85 (1 H, d, J = 2.3 Hz), 6.82 (1 H, dd, J = 2.3, 8.5 Hz), 5.22 (2 H, s), 3.94 (3 H, s) |
| 103 | (structure: 4-bromo-2-fluorobenzyl ether linked to 2-methoxyphenyl-imidazole-(3-chloro-4-fluorophenyl), HCl salt) | 237-243 | 8.55 (1 H, dd, J = 2.3, 6.8 Hz), 8.23-8.30 (1 H, m), 7.98 (1 H, d, J = 8.3 Hz), 7.86 (1 H, s), 7.72 (1 H, dd, J = 9.1, 9.1 Hz), 7.62 (1 H, dd, J = 1.7, 9.5 Hz), 7.56 (1 H, dd, J = 7.9, 9.5 Hz), 7.49 (1 H, dd, J = 1.7, 7.9 Hz), 6.77-6.87 (2 H, m), 5.20 (2 H, s), 3.93 (3 H, s) |

TABLE 5-continued

| Example No. | Structural Formula | Melting Point (° C.) | $^1$H-NMR (DMSO-$d_6$) |
|---|---|---|---|
| 104 | (4-chlorobenzyloxy)-OMe-phenyl-imidazole-(4-methoxyphenyl) | 170-173 | 12.30 (1 H, brs), 8.08 (1 H, d, J = 8.3 Hz), 7.93 (2 H, d, J = 8.3 Hz), 7.41-7.56 (5 H, m), 7.03 (2 H, d, J = 8.3 Hz), 6.65-6.78 (2 H, m), 5.14 (2 H, s), 3.90 (3 H, s), 3.80 (3 H, s) |
| 105 | HO-OMe-phenyl-imidazole·HCl-phenyl | 232-235 | 14.77 (1 H, brs), 10.12 (1 H, brs), 8.18-8.30 (2 H, m), 7.75-7.87 (2 H, m), 7.58-7.72 (3 H, m), 6.62 (1 H, s), 6.56 (1 H, d, J = 8.7 Hz), 3.89 (3 H, s) |
| 106 | HO-OMe-phenyl-imidazole-(4-CF$_3$-phenyl) | >250 | 12.73 (1 H, brs), 9.44 (1 H, brs), 8.20 (2 H, d, J = 8.3 Hz), 7.98 (1 H, d, J = 8.7 Hz), 7.83 (2 H, d, J = 8.3 Hz), 7.54 (1 H, s), 6.48 (1 H, s), 6.45 (1 H, d, J = 8.7 Hz), 3.87 (3 H, s) |
| 107 | HO-OMe-phenyl-imidazole·HCl-(4-fluorophenyl) | >250 | 14.78 (1 H, brs), 10.12 (1 H, brs), 8.27-8.39 (2 H, m), 7.82 (1 H, d, J = 8.7 Hz), 7.80 (1 H, s), 7.49-7.59 (2 H, m), 6.62 (1 H, d, J = 2.1 Hz), 6.55 (1 H, dd, J = 2.1, 8.7 Hz), 3.88 (3 H, s) |
| 108 | HO-OMe-phenyl-imidazole·HCl-(4-methylphenyl) | 260-262 | 14.64 (1 H, brs), 10.11 (1 H, s), 8.11 (2 H, d, J = 8.3 Hz), 7.78 (1 H, d, J = 8.3 Hz), 7.77 (1 H, s), 7.46 (2 H, d, J = 8.3 Hz), 6.62 (1 H, s), 6.55 (1 H, d, J = 8.3 Hz), 3.88 (3 H, s), 2.42 (3 H, s) |
| 109 | benzyloxy-OMe-phenyl-imidazole-(4-methylphenyl) | 219-222 | 14.68 (1 H, brs), 8.12 (2 H, d, J = 7.5 Hz), 7.94 (1 H, d, J = 8.3 Hz), 7.83 (1 H, s), 7.21-7.62 (7 H, m), 6.85 (1 H, s), 8.81 (1 H, d, J = 8.3 Hz), 5.21 (2 H, s), 3.93 (3 H, s), 2.42 (3 H, s) |
| 110 | (4-chlorobenzyloxy)-OMe-phenyl-imidazole-(3,4-dichlorophenyl) | 145-148 | 12.68 (1 H, brs), 8.23 (1 H, brs), 8.09 (1 H, d, J = 8.3 Hz), 7.99 (1 H, d, J = 8.3 Hz), 7.73 (1 H, d, J = 8.8 Hz), 7.58 (1 H, s), 7.52 (2 H, d, J = 8.8 Hz), 7.47 (2 H, d, J = 8.8 Hz), 6.73 (1 H, s), 6.70 (1 H, d, J = 8.8 Hz), 5.15 (2 H, s), 3.91 (3 H, s) |

TABLE 5-continued

| Example No. | Structural Formula | Melting Point (° C.) | ¹H-NMR (DMSO-d₆) |
|---|---|---|---|
| 111 | (structure) | 137-140 | 12.66 (1 H, brs), 8.24 (1 H, s), 8.07 (1 H, m), 8.00 (1 H, dd, J = 2.0, 8.3 Hz), 7.89 (2 H, d, J = 8.3 Hz), 7.73 (1 H, d, J = 8.3 Hz), 7.68 (2 H, d, J = 8.3 Hz), 7.56 (1 H, brs), 6.76 (1 H, s), 6.71 (1 H, d, J = 8.8 Hz), 5.27 (2 H, s), 3.91 (3 H, s) |
| 112 | (structure) | 252-257 | 8.47-8.56 (1 H, m), 8.15-8.22 (1 H, m), 8.02 (1 H, d, J = 8.8 Hz), 7.86 (1 H, s), 7.70-7.80 (1 H, m), 7.51 (2 H, d, J = 8.3 Hz), 7.46 (2 H, d, J = 8.3 Hz), 6.82 (1 H, d, J = 2.4 Hz), 6.77 (1 H, dd, J = 2.4, 8.8 Hz), 5.19 (2 H, s), 3.92 (3 H, s) |
| 113 | (structure) HCl | 223-226 | 8.45 (1 H, s), 8.26-8.30 (1 H, m), 8.03 (1 H, d, J = 8.8 Hz), 7.89 (1 H, s), 7.63-7.72 (2 H, m), 7.53 (2 H, d, J = 8.3 Hz), 7.48 (2 H, d, J = 8.3 Hz), 6.84 (1 H, d, J = 2.4 Hz), 6.80 (1 H, dd, J = 2.4, 8.8 Hz), 5.21 (2 H, s), 3.94 (3 H, s) |
| 114 | (structure) HCl | 217-220 | 8.14 (1 H, s), 8.08 (1 H, d, J = 8.3 Hz), 8.01 (1 H, d, J = 8.5 Hz), 7.81 (1 H, s), 7.40-7.55 (6 H, m), 6.82 (1 H, d, J = 2.2 Hz), 6.77 (1 H, dd, J = 2.2, 8.5 Hz), 5.19 (2 H, s), 3.92 (3 H, s), 2.40 (3 H, s) |
| 115 | (structure) | 154-157 | 12.41 (1 H, brs), 8.09 (1 H, d, J = 8.8 Hz), 7.92 (2 H, d, J = 8.3 Hz), 7.42-7.56 (7 H, m), 6.71 (1 H, s), 6.69 (1 H, d, J = 8.8 Hz), 5.14 (2 H, s), 3.90 (3 H, s), 1.31 (9 H, s) |
| 116 | (structure) | 177-184 | 12.41 (1 H, brs), 8.10 (1 H, d, J = 8.8 Hz), 7.93 (2 H, d, J = 7.8 Hz), 7.88 (2 H, d, J = 8.3 Hz), 7.68 (2 H, d, J = 8.3 Hz), 7.44-7.53 (3 H, m), 6.74 (1 H, s), 6.70 (1 H, d, J = 8.8 Hz), 5.26 (2 H, s), 3.91 (3 H, s), 1.31 (9 H, s) |

TABLE 5-continued

| Example No. | Structural Formula | Melting Point (° C.) | $^1$H-NMR (DMSO-$d_6$) |
| --- | --- | --- | --- |
| 117 | | 243-246 | 8.35 (1 H, s), 8.15 (1 H, s), 8.09 (1 H, d, J = 7.5 Hz), 8.02 (1 H, d, J = 8.5 Hz), 7.90 (2 H, d, J = 8.3 Hz), 7.85 (1 H, s), 7.69 (2 H, d, J = 8.3 Hz), 7.53 (1 H, dd, J = 7.5, 7.5 Hz), 7.46 (1 H, d, J = 7.5 Hz), 6.87 (1 H, d, J = 2.2 Hz), 6.80 (1 H, d, J = 2.2, 8.5 Hz), 5.33 (2 H, s), 3.94 (3 H, s), 2.42 (3 H, s) |
| 118 | | 233-241 | 8.46 (2 H, d, J = 1.9 Hz), 8.04 (1 H, d, J = 8.7 Hz), 7.87 (1 H, s), 7.83 (1 H, dd, J = 1.9 Hz), 7.50 (2 H, d, J = 8.8 Hz), 7.46 (2 H, d, J = 8.8 Hz), 6.81 (1 H, d, J = 2.4 Hz), 6.76 (1 H, dd, J = 2.4, 8.7 Hz), 5.19 (2 H, s), 3.92 (3 H, s) |
| 119 | | 231-236 | 8.73 (1 H, s), 8.64 (1 H, d, J = 8.1 Hz), 8.05 (1 H, d, J = 8.6 Hz), 7.99 (1 H, d, J = 8.1 Hz), 7.92 (1 H, s), 7.88 (1 H, dd, J = 7.8, 8.1 Hz), 7.53 (2 H, d, J = 8.6 Hz), 7.48 (2 H, d, J = 8.6 Hz), 6.86 (1 H, d, J = 2.2 Hz), 6.81 (1 H, dd, J = 2.2, 8.6 Hz), 5.22 (2 H, s), 3.95 (3 H, s) |
| 120 | | >250 | 8.42 (1 H, d, J = 1.8 Hz), 8.33 (1 H, s), 8.02 (1 H, d, J = 8.6 Hz), 7.88-7.92 (3 H, m), 7.69 (2 H, d, J = 8.3 Hz), 6.86 (1 H, d, J = 2.2 Hz), 6.80 (1 H, dd, J = 2.2, 8.6 Hz), 5.33 (2 H, s), 3.94 (3 H, s) |
| 121 | | 247-249 | 8.47-8.56 (1 H, m), 8.15-8.22 (1 H, m), 8.02 (1 H, d, J = 8.5 Hz), 7.88 (1 H, s), 7.77 (1 H, dd, J = 8.6, 19.0 Hz), 7.50 (2 H, d, J = 7.2 Hz), 7.42 (2 H, dd, J = 7.2, 7.2 Hz), 7.36 (1 H, dd, J = 7.2, 7.2 Hz), 6.84 (1 H, d, J = 2.1 Hz), 6.80 (1 H, d, J = 8.5 Hz), 5.21 (2 H, s), 3.93 (3 H, s) |
| 122 | | 142-145 | 12.64 (1 H, brs), 7.93-8.18 (3 H, m), 7.56 (1 H, s), 7.30-7.54 (7 H, m), 6.67-6.81 (2 H, m), 5.14 (2 H, s), 3.91 (3 H, s) |

TABLE 5-continued

| Example No. | Structural Formula | Melting Point (° C.) | ¹H-NMR (DMSO-d₆) |
|---|---|---|---|
| 123 | | 160-163 | 12.58 (1 H, brs), 7.98-8.12 (3 H, m), 7.46-7.57 (5 H, m), 7.31-7.45 (3 H, m), 6.66-6.79 (2 H, m), 5.14 (2 H, s), 3.90 (3 H, s) |
| 124 | | 242-245 | 8.62 (1 H, s), 8.26 (1 H, d, J = 8.6 Hz), 7.99 (1 H, d, J = 8.6 Hz), 7.91 (1 H, d, J = 8.6 Hz), 7.87 (1 H, s), 7.48 (2 H, d, J = 7.3 Hz), 7.40 (2 H, dd, J = 7.3, 7.3 Hz), 7.34 (1 H, d, J = 7.3 Hz), 6.82 (1 H, s), 6.78 (1 H, d, J = 8.6 Hz), 5.19 (2 H, s), 3.92 (3 H, s) |
| 125 | | 161-163 | 12.75 (1 H, brs), 7.99-8.17 (3 H, m), 7.30-7.67 (7 H, m), 6.68-6.78 (2 H, m), 5.15 (2 H, s), 3.91 (3 H, s) |
| 126 | | 159-162 | 12.75 (1 H, brs), 8.26-8.47 (2 H, m), 8.11 (1 H, d, J = 7.3 Hz), 7.64-7.78 (2 H, m), 7.60 (1 H, brs), 7.50 (2 H, d, J = 7.3 Hz), 7.41 (2 H, dd, J = 7.3, 7.3 Hz), 7.35 (1 H, d, J = 7.3 Hz), 6.68-6.79 (2 H, m), 5.15 (2 H, s), 3.91 (3 H, s) |
| 127 | | 194-196 | 8.15 (1 H, s), 8.09 (1 H, d, J = 7.9 Hz), 8.01 (1 H, d, J = 8.7 Hz), 7.84 (1 H, s), 7.32-7.58 (7 H, m), 6.85 (1 H, d, J = 2.4 Hz), 6.80 (1 H, dd, J = 2.4, 8.7 Hz), 5.21 (2 H, s), 3.94 (3 H, s), 2.43 (3 H, s) |
| 128 | | 154-165 | 8.24 (2 H, d, J = 9.2 Hz), 7.96 (1 H, d, J = 8.6 Hz), 7.79 (1 H, s), 7.50 (2 H, d, J = 7.3 Hz), 7.42 (2 H, dd, J = 7.3, 7.3 Hz), 7.37 (1 H, d, = 7.3 Hz), 7.20 (2 H, d, J = 9.2 Hz), 6.85 (1 H, d, J = 2.2 Hz), 6.80 (1 H, dd, J = 2.2, 8.6 Hz), 5.21 (2 H, s), 3.93 (3 H, s), 3.88 (3 H, s) |

TABLE 5-continued

| Example No. | Structural Formula | Melting Point (° C.) | ¹H-NMR (DMSO-d₆) |
|---|---|---|---|
| 129 | | 227-229 | 12.39 (1 H, s), 8.08 (1 H, d, J = 7.9 Hz), 7.91 (2 H, d, J = 8.3 Hz), 7.26-7.53 (8 H, m), 6.65-6.78 (2 H, m), 5.12 (2 H, s), 3.89 (3 H, s), 1.30 (9 H, s) |
| 130 | | 236-238 | 7.99 (1 H, d, J = 8.6 Hz), 7.91-7.96 (1 H, m), 7.85 (1 H, s), 7.84 (1 H, d, J = 8.1 Hz), 7.55 (1 H, dd, J = 8.1, 8.1 Hz), 7.50 (2 H, d, J = 7.3 Hz), 7.42 (2 H, dd, J = 7.3, 7.3 Hz), 7.37 (1 H, d, J = 7.3 Hz), 7.20 (1 H, dd, J = 2.2, 8.1 Hz), 6.85 (1 H, d, J = 2.2 Hz), 6.80 (1 H, dd, J = 2.2, 8.6 Hz), 5.21 (2 H, s), 3.93 (3 H, s), 3.90 (3 H, s) |
| 131 | | 191-194 | 12.59 (1 H, brs), 8.09 (1 H, d, J = 8.3 Hz), 8.01 (1 H, d, J = 8.3 Hz), 7.64 (1 H, dd, J = 8.3, 8.3 Hz), 7.47-7.58 (4 H, m), 7.36 (1 H, d, J = 8.3 Hz), 6.68-6.79 (2 H, m), 5.17 (2 H, s), 3.91 (3 H, s) |
| 132 | | 165-166 | 12.79 (1 H, brs), 8.22 (2 H, d, J = 7.8 Hz), 8.10 (1 H, s), 7.83 (2 H, d, J = 7.8 Hz), 7.64 (1 H, dd, J = 8.3, 8.3 Hz), 7.58 (1 H, brs), 7.52 (1 H, dd, J = 2.1, 10.0 Hz), 7.36 (1 H, d, J = 8.3 Hz), 6.67-6.81 (2 H, m), 5.18 (2 H, s), 3.92 (3 H, s) |
| 133 | | 259-260 | 8.25-8.32 (2 H, m), 7.95 (1 H, d, J = 8.3 Hz), 7.88 (1 H, s), 7.65 (1 H, dd, J = 8.3, 8.3 Hz), 7.50-7.58 (3 H, m), 7.38 (1 H, dd, J = 2.0, 8.3 Hz), 6.82-6.89 (2 H, m), 5.24 (2 H, s), 3.94 (3 H, s) |
| 134 | | 245-249 | 7.95 (1 H, d, J = 8.3 Hz), 7.88 (1 H, s), 7.84-7.87 (1 H, m), 7.78 (1 H, d, J = 8.3 Hz), 7.65 (1 H, dd, J = 8.3, 8.3 Hz), 7.50-7.59 (2 H, m), 7.38 (1 H, dd, J = 2.4, 8.3 Hz), 7.20 (1 H, dd, J = 2.4, 8.3 Hz), 6.87 (1 H, d, J = 2.4 Hz), 6.84 (1 H, dd, J = 2.4, 8.3 Hz), 5.24 (2 H, s), 3.94 (3 H, s), 3.89 (3 H, s) |

TABLE 5-continued

| Example No. | Structural Formula | Melting Point (° C.) | ¹H-NMR (DMSO-d₆) |
|---|---|---|---|
| 135 | | 115-120 | 12.45 (1 H, brs), 8.03 (1 H, d, J = 7.8 Hz), 7.85 (1 H, s), 7.80 (1 H, d, J = 7.8 Hz), 7.64 (1 H, dd, J = 8.3, 8.3 Hz), 7.51 (1 H, dd, J = 2.0, 10.2 Hz), 7.48 (1 H, s), 7.31-7.38 (2 H, m), 7.17 (1 H, d, J = 7.8 Hz), 6.74 (1 H, s), 6.71 (1 H, d, J = 2.4 Hz), 5.17 (2 H, s), 3.91 (3 H, s), 2.38 (3 H, s) |
| 136 | | 152-155 | 12.37 (1 H, brs), 8.02 (1 H, brs), 7.90 (2 H, d, J = 8.3 Hz), 7.64 (1 H, dd, J = 8.0, 8.0 Hz), 7.51 (1 H, dd, J = 2.0, 9.8 Hz), 7.46 (1 H, s), 7.36 (1 H, dd, J = 2.0, 8.0 Hz), 7.27 (2 H, d, J = 8.3 Hz), 6.73 (1 H, s), 6.71 (1 H, d, J = 2.4 Hz), 5.17 (2 H, s), 3.90 (3 H, s), 2.34 (3 H, s) |
| 137 | | 251-255 | 8.37 (1 H, m), 8.08-8.17 (1 H, m), 7.98 (1 H, d, J = 8.3 Hz), 7.90 (1 H, s), 7.72-7.83 (1 H, m), 7.65 (1 H, d, J = 8.3 Hz), 7.53 (1 H, dd, J = 2.0, 10.2 Hz), 7.38 (1 H, d, J = 8.3 Hz), 6.81-6.89 (2 H, m), 5.24 (2 H, s), 3.94 (3 H, s) |
| 138 | | 254-258 | 8.57 (1 H, d, J = 2.2 Hz), 8.22 (1 H, dd, J = 2.2, 8.5 Hz), 7.98 (1 H, d, J = 8.3 Hz), 7.94 (1 H, d, J = 8.5 Hz), 7.90 (1 H, s), 7.65 (1 H, d, J = 8.3 Hz), 7.53 (1 H, dd, J = 2.0, 9.8 Hz), 7.38 (1 H, d, J = 8.3 Hz), 6.81-6.87 (2 H, m), 5.23 (2 H, s), 3.94 (3 H, s) |
| 139 | | 249-251 | 8.25 (2 H, dd, J = 2.9, 6.3 Hz), 7.99 (1 H, d, J = 8.5 Hz), 7.88 (1 H, s), 7.62-7.70 (4 H, m), 7.53 (1 H, dd, J = 2.0, 10.2 Hz), 7.37 (1 H, dd, J = 2.0, 8.0 Hz), 6.87 (1 H, d, J = 2.2 Hz), 6.84 (1 H, dd, J = 2.2, 8.5 Hz), 5.24 (2 H, s), 3.95 (3 H, s) |

Examples 140 to 188
The compound of the present invention was produced in the same manner as in Example 1, using appropriate starting materials. Table 6 shows the structures of the obtained compounds.
TABLE 6
| Example No. | Structural Formula |
|---|---|
| 140 | 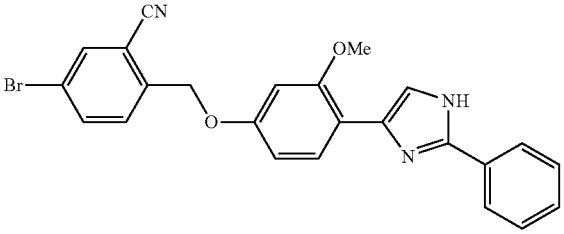 |
| 141 | 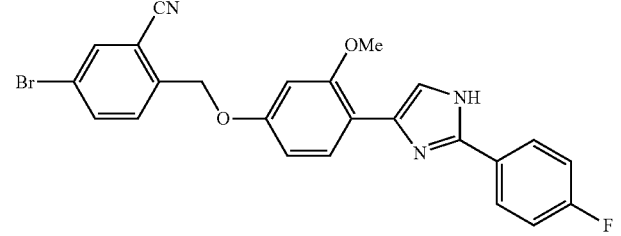 |
| 142 | 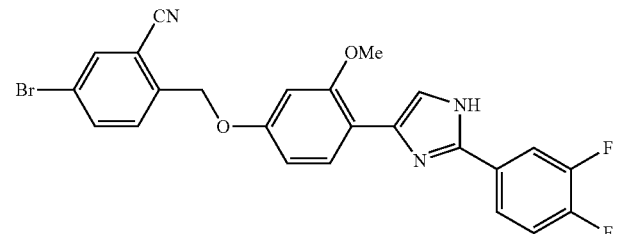 |
| 143 | 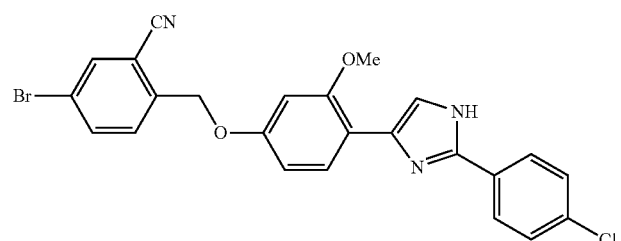 |
| 144 | 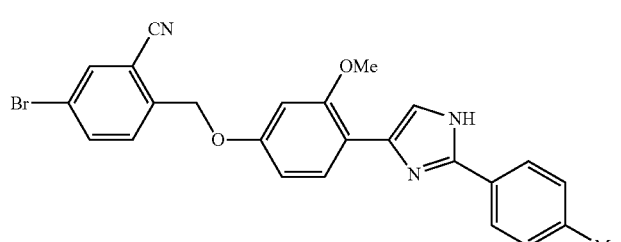 |

TABLE 6-continued
| Example No. | Structural Formula |
|---|---|
| 145 | 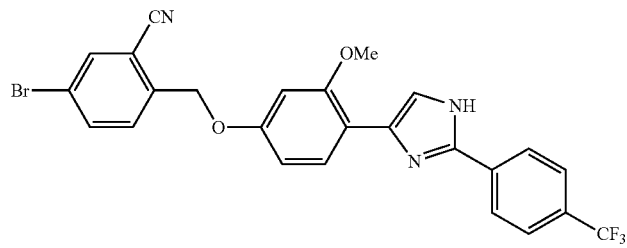 |
| 146 | 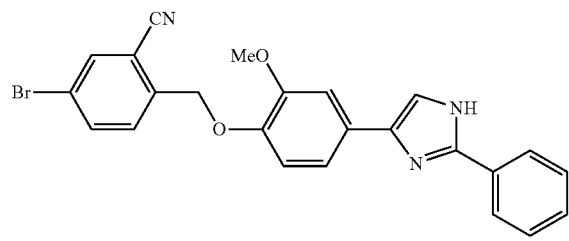 |
| 147 | 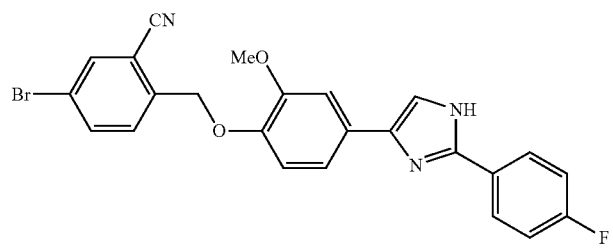 |
| 148 | 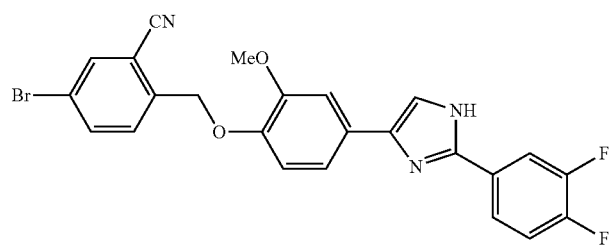 |
| 149 | 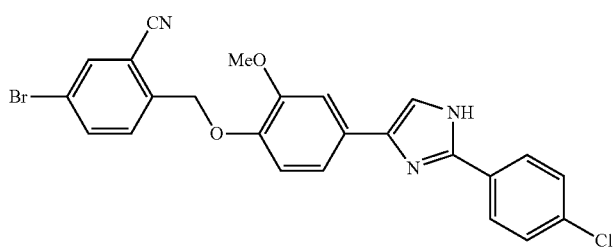 |
| 150 | 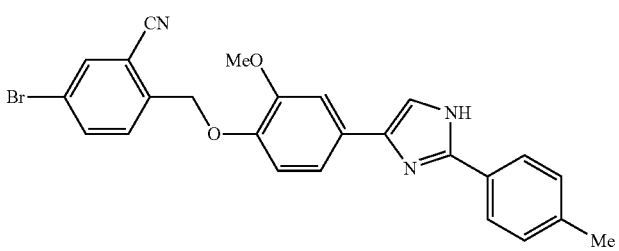 |

TABLE 6-continued

| Example No. | Structural Formula |
|---|---|
| 151 | 5-bromo-2-({[3-methoxy-4-(2-(4-(trifluoromethyl)phenyl)-1H-imidazol-4-yl)phenoxy]methyl})benzonitrile |
| 152 | 2-({[3-methoxy-4-(2-phenyl-1H-imidazol-4-yl)phenoxy]methyl})-5-(trifluoromethyl)pyridine |
| 153 | 2-({[4-(2-(4-fluorophenyl)-1H-imidazol-4-yl)-3-methoxyphenoxy]methyl})-5-(trifluoromethyl)pyridine |
| 154 | 2-({[4-(2-(3,4-difluorophenyl)-1H-imidazol-4-yl)-3-methoxyphenoxy]methyl})-5-(trifluoromethyl)pyridine |
| 155 | 2-({[4-(2-(4-chlorophenyl)-1H-imidazol-4-yl)-3-methoxyphenoxy]methyl})-5-(trifluoromethyl)pyridine |
| 156 | 2-({[3-methoxy-4-(2-(p-tolyl)-1H-imidazol-4-yl)phenoxy]methyl})-5-(trifluoromethyl)pyridine |
| 157 | 2-({[3-methoxy-4-(2-(4-(trifluoromethyl)phenyl)-1H-imidazol-4-yl)phenoxy]methyl})-5-(trifluoromethyl)pyridine |

TABLE 6-continued
| Example No. | Structural Formula | |
|---|---|---|
| 158 | 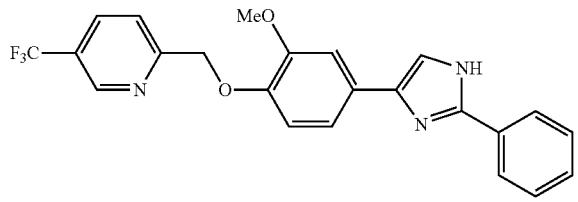 | |
| 159 | 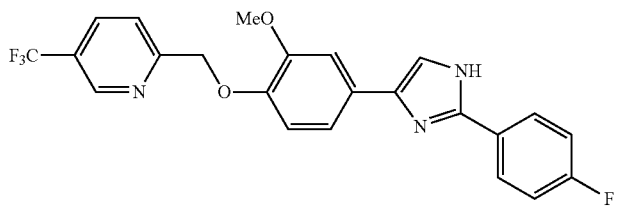 | |
| 160 | 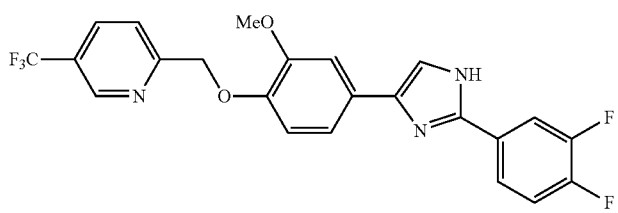 | |
| 161 | 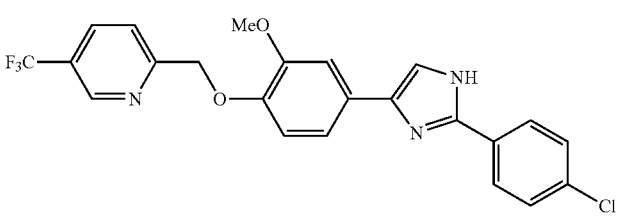 | |
| 162 | 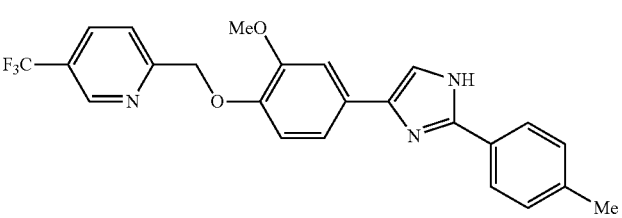 | |
| 163 | 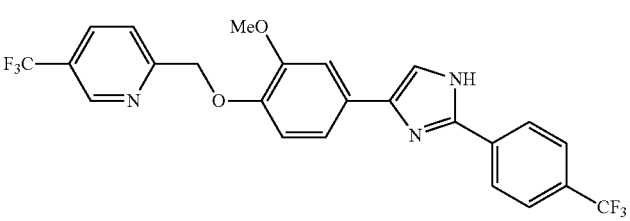 | |
| 164 | 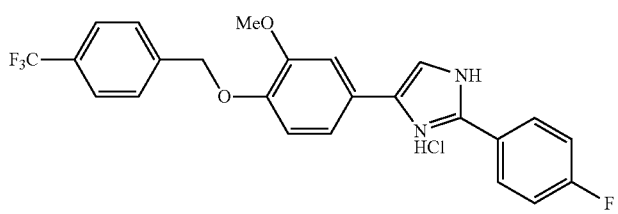 | 242-245 8.40(2H, dd, J = 5.1, 9.0 Hz), 8.21(1H, s), 7.76-7.80(3H, m), 7.69(2H, d, J = 8.3 Hz), 7.51-7.58(3H, m), 7.18(1H, d, J = 8.3 Hz), 5.19(2H, s), 3.93(3H, s) |

TABLE 6-continued

| Example No. | Structural Formula | | |
|---|---|---|---|
| 165 | [4-(trifluoromethyl)benzyl ether of 3-methoxy-4-hydroxyphenyl imidazole with 4-CF3 phenyl] | 130-132 | 12.89(1H, s), 8.20(2H, d, J = 7.8 Hz), 7.84(2H, d, J = 7.8 Hz), 7.81(1H, s), 7.78(2H, d, J = 7.8 Hz), 7.69(2H, d, J = 7.8 Hz), 7.51(1H, s), 7.40(1H, d, J = 8.3 Hz), 7.06(1H, d, J = 8.3 Hz), 5.23(2H, s), 3.88(3H, s) |
| 166 | [4-(trifluoromethyl)benzyl ether of 2-methoxy-4-hydroxyphenyl imidazole with 4-F phenyl] | 176-179 | 12.49(1H, s), 8.09(1H, d, J = 8.5 Hz), 8.04(2H, dd, J = 5.6, 8.8 Hz), 7.78(2H, d, J = 8.3 Hz), 7.71(2H, d, J = 8.3 Hz), 7.52(1H, s), 7.31(2H, J = 8.8, 8.8 Hz), 6.75(1H, d, J = 2.2 Hz), 6.71(1H, dd, J = 2.2, 8.5 Hz), 5.27(2H, s), 3.91(3H, s) |
| 167 | [4-(trifluoromethyl)benzyl ether of 2-methoxy-4-hydroxyphenyl imidazole with 4-CF3 phenyl] | 177-179 | 12.78(1H, s), 8.22(2H, d, J = 8.3 Hz), 8.11(1H, d, J = 7.8 Hz), 7.83(2H, d, J = 8.3 Hz), 7.78(2H, d, J = 7.8 Hz), 7.72(2H, d, J = 7.8 Hz), 7.61(1H, s), 6.77(1H, s), 6.73(1H, d, J = 7.8 Hz), 5.28(2H, s), 3.92(3H, s) |
| 168 | [pyridin-2-ylmethyl ether of 3-methoxy-4-hydroxyphenyl imidazole with 4-F phenyl] | 164-167 | 12.59(1H, s), 8.58(1H, d, J = 4.1 Hz), 7.98-8.11(2H, m), 7.85(1H, ddd, J = 1.7, 7.5, 7.5 Hz), 7.69(1H, s), 7.55(1H, d, J = 7.5 Hz), 7.49(1H, s), 7.25-7.42(4H, m), 7.03(1H, d, J = 7.9 Hz), 5.18(2H, s), 3.88(3H, s) |
| 169 | [pyridin-2-ylmethyl ether of 3-methoxy-4-hydroxyphenyl imidazole with 4-CF3 phenyl] | 226-227 | 8.58-8.60(1H, m), 8.21(2H, d, J = 7.9 Hz), 7.82-7.88(3H, m), 7.74(1H, brs), 7.56(1H, d, J = 7.9 Hz), 7.49(1H, s), 7.34-7.39(2H, m), 7.07(1H, d, J = 7.9 Hz), 5.19(2H, s), 3.89(3H, s) |
| 170 | [pyridin-2-ylmethyl ether of 2-methoxy-4-hydroxyphenyl imidazole with 4-F phenyl, HCl salt] | 254-257 | 8.78(1H, d, J = 4.6 Hz), 8.40(2H, dd, J = 5.2, 8.9 Hz), 8.23(1H, dd, J = 6.4, 7.9 Hz), 8.06(1H, d, J = 8.5 Hz), 7.88(1H, s), 7.86(1H, d, J = 7.9 Hz), 7.69(1H, dd, J = 4.6, 6.4 Hz), 7.54(2H, dd, J = 8.9, 8.9 Hz), 6.94(1H, d, J = 2.5 Hz), 6.85(1H, dd, J = 2.5, 8.5 Hz), 5.47(2H, s), 3.95(3H, s) |
| 171 | [pyridin-2-ylmethyl ether of 2-methoxy-4-hydroxyphenyl imidazole with 4-CF3 phenyl, HCl salt] | 255-258 | 8.82(1H, d, J = 5.0 Hz), 8.55(1H, d, J = 8.3 Hz), 8.31(1H, dd, J = 7.5, 7.5 Hz), 8.12(1H, d, J = 8.3 Hz), 8.05(2H, d, J = 8.3 Hz), 7.97(1H, s), 7.93(1H, d, J = 7.5 Hz), 7.77(1H, dd, J = 5.0, 7.5 Hz), 6.95(1H, d, J = 2.1 Hz), 6.87(1H, dd, J = 2.1, 8.3 Hz), 5.52(2H, s), 3.97(3H, s) |

TABLE 6-continued
| Example No. | Structural Formula |
|---|---|
| 172 | 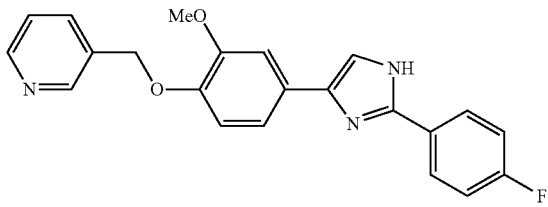 |
| 173 | 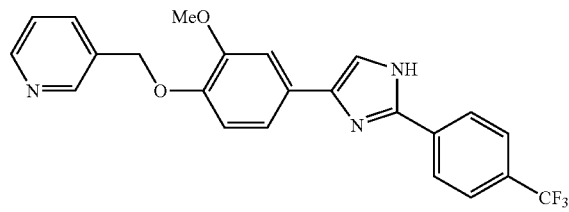 |
| 174 | 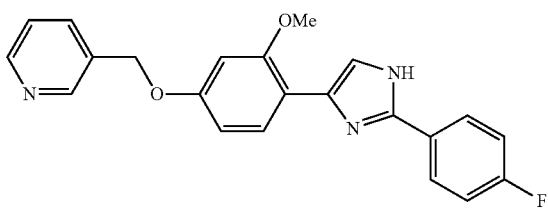 |
| 175 | 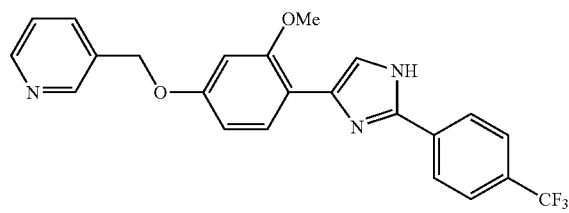 |
| 176 | 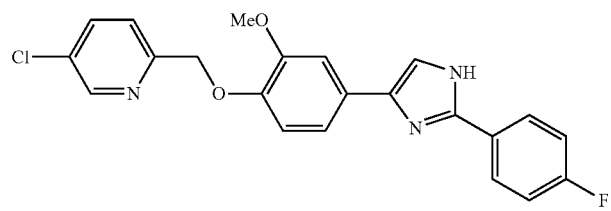 |
| 177 | 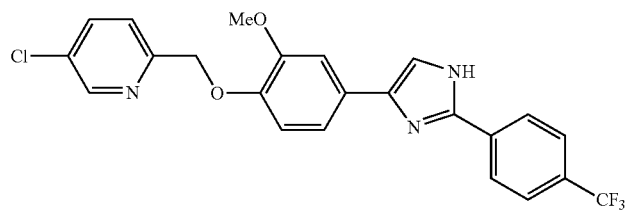 |
| 178 | 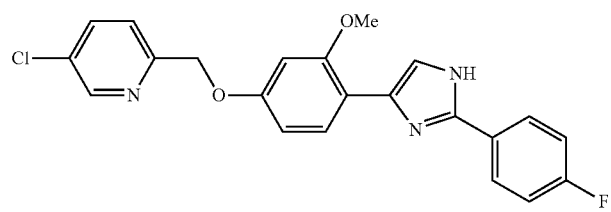 |

TABLE 6-continued

| Example No. | Structural Formula | | |
|---|---|---|---|
| 179 | [5-chloropyridin-2-yl-methoxy, 2-methoxyphenyl, 2-(4-trifluoromethylphenyl)-1H-imidazole] | | |
| 180 | [5-cyanopyridin-2-yl-methoxy, 3-methoxyphenyl, 2-(4-fluorophenyl)-1H-imidazole] | | |
| 181 | [5-cyanopyridin-2-yl-methoxy, 2-methoxyphenyl, 2-(4-trifluoromethylphenyl)-1H-imidazole] | | |
| 182 | [5-cyanopyridin-2-yl-methoxy, 3-methoxyphenyl, 2-(4-fluorophenyl)-1H-imidazole] | | |
| 183 | [5-cyanopyridin-2-yl-methoxy, 2-methoxyphenyl, 2-(4-trifluoromethylphenyl)-1H-imidazole] | | |
| 184 | [6-trifluoromethylpyridin-3-yl-methoxy, 3-methoxyphenyl, 2-(4-fluorophenyl)-1H-imidazole·HCl] | 248-252 | 8.85(1H, s), 8.46(2H, d, J = 8.3 Hz), 8.24(1H, s), 8.15(1H, d, J = 7.8 Hz), 8.01(2H, d, J = 8.3 Hz), 7.95(1H, d, J = 7.8 Hz), 7.71(1H, s), 7.55(1H, d, J = 8.3 Hz), 7.21(1H, d, J = 8.3 Hz), 5.32(2H, s), 3.90(3H, s) |
| 185 | [6-trifluoromethylpyridin-3-yl-methoxy, 3-methoxyphenyl, 2-(4-trifluoromethylphenyl)-1H-imidazole·HCl] | 252-254 | 8.88(1H, s), 8.40(2H, dd, J = 5.1, 9.0 Hz), 8.23(1H, s), 8.17(1H, d, J = 7.8 Hz), 7.98(1H, d, J = 7.8 Hz), 7.77(1H, d, J = 2.0 Hz), 7.58(1H, dd, J = 2.0, 8.3 Hz), 7.54(2H, dd, J = 9.0, 9.0 Hz), 7.24(1H, d, J = 8.3 Hz), 5.35(2H, s), 3.92(3H, s) |

TABLE 6-continued

| Example No. | Structural Formula | | |
|---|---|---|---|
| 186 | F₃C-phenyl-CH₂-O-phenyl(MeO)-imidazole(NH,HCl)-phenyl(3,4-diF) | 252-254 | 8.55(1H, ddd, J = 2.1, 7.5, 11.6 Hz), 8.19-8.23(2H, m), 7.74-7.81(4H, m), 7.69(2H, d, J = 7.9 Hz), 7.56(1H, dd, J = 2.1, 8.3 Hz), 7.18(1H, d, J = 8.3 Hz), 5.29(2H, s), 3.92(3H, s) |
| 187 | F₃C-phenyl-CH₂-O-phenyl(OMe)-imidazole(NH)-phenyl(4-Cl) | 180-182 | 12.58(1H, s), 8.09(1H, d, J = 8.5 Hz), 8.02(2H, d, J = 8.3 Hz), 7.78(2H, d, J = 8.3 Hz), 7.71(2H, d, J = 8.3 Hz), 7.52-7.55(3H, m), 6.75(1H, d, J = 2.2 Hz), 6.71(1H, dd, J = 2.2, 8.5 Hz), 5.27(2H, s), 3.91(3H, s) |
| 188 | F₃C-phenyl-CH₂-O-phenyl(OMe)-imidazole(NH,HCl)-phenyl(3,4-diF) | >250 | 8.50(1H, ddd, J = 1.8, 7.7, 11.6 Hz), 8.17-8.20(1H, m), 8.02(1H, d, J = 8.5 Hz), 7.89(1H, s), 7.71-7.80(5H, m), 6.87(1H, d, J = 2.0 Hz), 6.81(1H, dd, J = 2.0, 8.5 Hz), 5.34(2H, s), 3.94(3H, s) |

Test Example 1

Confirmation Test of LPL Activation Effect in Human Skeletal Muscle Cells and Mouse Skeletal Muscle Cells Human skeletal muscle cells (human skeletal muscle myoblasts) or mouse skeletal muscle cells (C2C12 cells) that were seeded onto plates, cultured, and differentiated were exposed to a 0.3% dimethyl sulfoxide-containing culture medium in which the compound of the present invention was dissolved (concentration: 10 μM or 30 μM). The medium was removed 8 hours after exposure, 10 mM of Tris-HCl buffer (150 mM NaCl, 10 μ/mL; containing heparin sodium) was added to the cells, and the cells were incubated at 37° C. in the presence of 5% $CO_2$ for 10 minutes. LPL activity in the supernatant was measured using an LPL activity assay kit (made by Roar Biomedical Inc.). LPL activity was evaluated based on the increase in fluorescence intensity 10 to 70 minutes after mixing the supernatant with the LPL substrate. The mean value of the increase in fluorescence intensity of the cells exposed to a 0.3% dimethyl sulfoxide-containing culture medium of the present invention was used as mean value of the control group. Note that the compounds of Examples 18, 19, 32, 45 and 57 were tested using human skeletal muscle cells, and other compounds were tested using mouse skeletal muscle cells.

The rate of increase (%) was calculated from the measured values of LPL activity in the control group and the experimental group, according to the following formula.

Rate of increase in LPL activity (%)=[(mean value of the experimental group)−(mean value of the control group)]/(mean value of the control group)×100

Table 7 shows the results.

TABLE 7

| | Amount of Addition | |
|---|---|---|
| Example No. | 10 μM | 30 μM |
| 1 | 64 | 360 |
| 2 | 13 | 38 |
| 3 | 43 | 62 |
| 4 | 31 | 45 |
| 5 | 14 | 42 |
| 7 | 69 | 197 |
| 10 | 46 | 275 |
| 11 | 96 | 231 |
| 13 | 46 | 234 |
| 15 | 79 | 97 |
| 16 | 54 | 119 |
| 17 | 81 | 143 |
| 18 | 23 | 23 |
| 19 | 24 | 28 |
| 23 | 40 | 95 |
| 24 | 59 | 77 |
| 26 | 31 | 51 |
| 28 | 30 | 53 |
| 30 | 11 | 47 |
| 31 | 10 | 38 |
| 32 | 22 | 57 |
| 33 | 60 | 84 |
| 36 | 6 | 113 |
| 38 | 35 | 100 |
| 42 | 47 | 131 |
| 43 | 64 | 157 |
| 45 | 23 | 32 |
| 46 | 49 | 88 |
| 47 | 38 | 120 |
| 48 | 18 | 96 |
| 49 | 47 | 147 |

TABLE 7-continued

| Example No. | Amount of Addition 10 μM | 30 μM |
|---|---|---|
| 50 | 20 | 70 |
| 51 | 16 | 115 |
| 54 | 18 | 87 |
| 55 | 49 | 94 |
| 56 | 38 | 62 |
| 57 | 19 | 40 |
| 58 | 45 | 150 |
| 59 | 22 | 73 |
| 61 | 53 | 92 |
| 65 | 24 | 46 |
| 66 | 24 | 32 |
| 67 | 22 | 34 |
| 68 | 10 | 289 |
| 69 | 52 | 142 |
| 70 | 22 | 87 |
| 71 | 42 | 114 |
| 72 | 70 | 123 |
| 73 | 55 | 108 |
| 74 | 10 | 55 |
| 75 | 43 | 89 |
| 76 | 115 | 263 |
| 77 | 54 | 133 |
| 78 | 14 | 60 |
| 79 | 16 | 64 |
| 80 | 21 | 302 |
| 81 | 32 | 89 |
| 82 | 27 | 86 |
| 83 | 29 | 100 |
| 84 | 53 | 97 |
| 85 | 10 | 99 |
| 86 | 40 | 375 |
| 87 | 23 | 144 |
| 88 | 12 | 98 |
| 90 | 18 | 130 |
| 91 | 28 | 95 |
| 92 | 42 | 123 |
| 93 | 36 | 174 |
| 94 | 9 | 15 |
| 96 | 27 | 96 |
| 97 | 27 | 63 |
| 99 | 14 | 90 |
| 100 | 12 | 43 |
| 102 | 44 | 88 |
| 103 | 30 | 92 |
| 104 | 74 | 365 |
| 109 | 12 | 77 |
| 110 | 37 | 106 |
| 111 | 61 | 81 |
| 112 | 58 | 199 |
| 113 | 4 | 123 |
| 115 | 62 | 88 |
| 116 | 36 | 84 |
| 118 | 80 | 102 |
| 119 | 67 | 174 |
| 121 | 113 | 270 |
| 123 | 11 | 42 |
| 124 | 93 | 113 |
| 126 | 99 | 297 |
| 128 | 49 | 208 |
| 130 | 9 | 170 |
| 132 | 35 | 213 |
| 133 | 63 | 236 |
| 134 | 32 | 308 |
| 139 | 71 | 128 |
| 164 | 4 | 228 |
| 165 | 38 | 476 |
| 167 | 37 | 104 |

Table 7 indicates an increase in LPL activity caused by the compound of the present invention.

Test Example 2

Confirmation Test of Lipid-Improving Action and Body Weight Gain-Inhibiting Effect 8-week-old SD rats (Japan Charles River: average body weight of about 350 g) were used. 5% aqueous gum arabic suspension, which was prepared such that the dosage of a compound of the present invention was 100 mg/kg body weight, was orally administered to the experimental group in an amount of 5 ml/kg body weight. 5% aqueous gum arabic suspension (not containing any compounds of the present invention) was orally administered to the control group in an amount of 5 ml/kg body weight. The rats were grouped according to their body weight at 8 weeks of age such that each group had 5 rats. The test compounds were orally administered every day at a fixed time for 5 days or 2 weeks, starting when the rats were 9 weeks old. Body weight was regularly measured during the period of oral administration, and the body weight gain-inhibiting effect was observed. 4 hours after the final administration of the test compound, blood was collected from the vein, plasma was separated from the collected blood, and blood biochemical examinations (triglyceride, HDL-cholesterol) were carried out.

The rate of inhibition of body weight gain (%) was calculated from the measured body weights of rats in the control group and the experimental group, according to the following formula. Table 8 shows the results.

Rate of inhibition of body weight gain (%)=[(mean value of the control group)−(mean value of the experimental group)]/(mean value of the control group)×100

Blood biochemical examinations of rats in the control group and the experimental group were performed. The rates of change (%) were calculated according to the following formulae from the measured values obtained from the blood biochemical examinations. Table 8 shows the results.

Rate of decrease in triglyceride levels (%)=[(mean value of the control group)−(mean value of the experimental group)]/(mean value of the control group)×100

Rate of increase in HDL-cholesterol levels (%)=[(mean value of the experimental group)−(mean value of the control group)]/(mean value of the control group)×100

TABLE 8

Effect on Body Weight

| Example No. | Rate of inhibition of body weight gain (%) |
|---|---|
| 18 | 13 |
| 19 | 11 |
| 32 | 8 |
| 45 | 12 |
| 52 | 6 |
| 57 | 14 |
| 67 | 7 |
| 70 | 14 |
| 74 | 6 |
| 84 | 8 |

Table 8 confirmed that the compound of the present invention has a body weight gain-inhibiting effect in normal rats.

TABLE 9

| Example No. | Rate of increase in triglyceride levels (%) | Rate of increase in HDL-cholesterol levels (%) |
|---|---|---|
| 18 | 69 | 171 |
| 19 | 79 | 99 |
| 32 | 57 | 16 |
| 45 | 51 | 27 |
| 52 | 62 | 36 |
| 57 | 88 | 184 |
| 67 | 40 | 15 |
| 70 | 64 | 34 |
| 74 | 46 | 64 |
| 84 | 48 | 187 |

Table 9 confirmed that the compound of the present invention has the effect of lowering triglyceride levels in the blood and the effect of increasing HDL cholesterol (good cholesterol) levels. An excessive increased in the triglyceride levels in the blood can cause hyperlipidemia and arteriosclerosis. On the other hand, an increase in HDL cholesterol levels can inhibit the onset of hyperlipidemia and arteriosclerosis. Accordingly, these results suggested that the compound of the present invention is effective in the prevention and treatment of hyperlipidemia and arteriosclerosis.

Test Example 3

Confirmation Test of Anti-Obesity Action in Dietary-Obese Mice

AKR/J mice were used. These mice were fed a high-fat diet with 60% kcal fat, and a model of dietary obesity was developed. 5% aqueous gum arabic suspension, which was prepared such that the dosage of a compound of the present invention was 20 mg/kg body weight, was orally administered to the experimental group of obese mice in an amount of 5 ml/kg body weight. 5% aqueous gum arabic suspension that does not contain any of the compounds of the present invention was administered to the control group in an amount of 5 ml/kg body weight. The mice were grouped according to body weight. The test suspension was administered everyday at a fixed time for 4 weeks. Body weight was measured during the period of oral administration, and the body weight gain-inhibiting effect was confirmed. The rate of body weight reduction (%) was calculated from the measured body weights of mice in the control group and the experimental group, according to the following formula. Table 10 shows the results.

Rate of body weight reduction (%)=[(mean value of the control group)−(mean value of the experimental group)]/(mean value of the control group)×100

TABLE 10

Effect in Dietary Obese Mice

| Example No. | Rate of body weight reduction (%) |
|---|---|
| 23 | 13 |
| 32 | 11 |
| 45 | 11 |
| 57 | 17 |

Table 10 indicates the effect of body weight reduction was also observed in a model of obese mice. Accordingly, the compound of the present invention was confirmed to be effective in alleviating obesity.

Preparation Example 1

Preparation of Tablets

Using the compound obtained in Example 18 as an active ingredient, tablets (10000 tablets) each containing 300 mg of the compound were prepared according to the following formulation.

| | |
|---|---|
| Compound obtained in Example 18 | 3000 g |
| Lactose (product of Japanese Pharmacopeia) | 335 g |
| Cornstarch (product of Japanese Pharmacopeia) | 165 g |
| Carboxymethylcellulose calcium (product of Japanese Pharmacopeia) | 125 g |
| Methylcellulose (product of Japanese Pharmacopeia) | 60 g |
| Magnesium stearate (product of Japanese Pharmacopeia) | 15 g |

According to the above formulation, the compound obtained in Example 18, lactose, cornstarch and carboxymethylcellulose calcium were sufficiently mixed. The mixture was granulated using a methylcellulose aqueous solution, screened with a 24-mesh screen, mixed with magnesium stearate, and pressed into tablets, thereby yielding the desired tablets.

Preparation Example 2

Preparation of Capsules

Using the compound obtained in Example 57 as an active ingredient, hard gelatin capsules (10000 capsules) each containing 200 mg of the compound were prepared according to the following formulation.

| | |
|---|---|
| Compound obtained in Example 57 | 2000 g |
| Crystalline cellulose (product of Japanese Pharmacopeia) | 300 g |
| Cornstarch (product of Japanese Pharmacopeia) | 170 g |
| Talc (product of Japanese Pharmacopeia) | 20 g |
| Magnesium stearate (product of Japanese Pharmacopeia) | 10 g |

According to the above formulation, each of the components was ground into a fine powder, and the powders were mixed to form a uniform mixture and loaded into gelatin capsules of a desired size for oral administration, thereby yielding the desired capsules.

The invention claimed is:
1. A phenylimidazole compound represented by the following General Formula (1):

[Chem. 1]

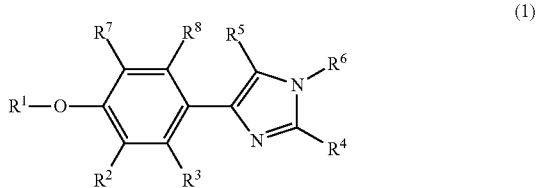

(1)

wherein $R^1$ represents a hydrogen atom, a phenyl lower alkyl group or a pyridyl lower alkyl group, and the benzene ring and the pyridine ring are optionally substituted with 1 or 2 substituents selected from the group consisting of halogen atoms, cyano group and halogen-substituted lower alkyl groups; one of $R^2$ and $R^3$ represents a hydrogen atom and the other represents a lower alkoxy group; $R^4$ represents a lower alkyl group, a furyl group, a thienyl group or a phenyl group optionally substituted with 1 or 2 substituents selected from the group consisting of lower alkyl groups, lower alkoxy groups, halogen atoms, carboxyl group, lower alkoxycarbonyl groups and halogen-substituted lower alkyl groups; $R^5$ and $R^6$ are the same or different, and represent a hydrogen atom or a lower alkyl group; $R^7$ and $R^8$ are the same or different, and represent a hydrogen atom or a lower alkoxy group; however, when $R^1$ represents an unsubstituted phenyl lower alkyl group, $R^2$ represents a lower alkoxy group, $R^3$ represents a hydrogen atom, $R^4$ represents an unsubstituted phenyl group or a phenyl group having 1 or 2 halogen-substituted lower alkyl groups, and $R^5$ represents a hydrogen atom, $R^6$ is not a hydrogen atom.

2. The phenylimidazole compound according to claim 1, wherein $R^7$ and $R^8$ represent a hydrogen atom in General Formula (1).

3. The phenylimidazole compound according to claim 1, wherein $R^4$ represents a thienyl group in General Formula (1).

4. The phenylimidazole compound according to claim 1, wherein $R^4$ represents a furyl group in General Formula (1).

5. The phenylimidazole compound according to claim 1, wherein, in General Formula (1), $R^4$ represents a phenyl group optionally substituted with 1 or 2 substituents selected from the group consisting of lower alkyl groups, lower alkoxy groups, halogen atoms, carboxyl group, lower alkoxycarbonyl groups and halogen-substituted lower alkyl groups.

6. The phenylimidazole compound according to claim 1, wherein, in General Formula (1), $R^1$ is an unsubstituted phenyl lower alkyl group or a phenyl lower alkyl group substituted with 1 or 2 substituents selected from the group consisting of halogen atoms, cyano group and halogen-substituted lower alkyl groups.

7. The phenylimidazole compound according to claim 6, wherein, in General Formula (1), $R^1$ is a group selected from the group consisting of benzyl, 4-cyanobenzyl, 3-cyanobenzyl, 2-cyanobenzyl, 4-chlorobenzyl, 4-trifluoromethylbenzyl, 4-chloro-2-fluorobenzyl and 4-bromo-2-fluorobenzyl.

8. The phenylimidazole compound according to claim 6, wherein, in General Formula (1), $R^1$ is a group selected from the group consisting of benzyl, 4-cyanobenzyl, 3-cyanobenzyl, 2-cyanobenzyl, 4-chlorobenzyl and 4-bromo-2-fluorobenzyl.

9. The phenylimidazole compound according to claim 1, wherein, in General Formula (1), $R^4$ is a thienyl group, a furyl group or a phenyl group optionally substituted with 1 or 2 substituents selected from the group consisting of lower alkyl groups, lower alkoxy groups, halogen atoms, lower alkoxycarbonyl groups and halogen-substituted lower alkyl groups.

10. The phenylimidazole compound according to claim 1, wherein, in General Formula (1), $R^4$ is a group selected from the group consisting of 2-thienyl, 3-thienyl, 3-furyl, phenyl, 4-fluorophenyl, 3-fluorophenyl, 3-fluoro-4-methylphenyl, 3,4-difluorophenyl, 4-trifluoromethylphenyl, 3-trifluoromethylphenyl, 2-trifluoromethylphenyl, 4-chlorophenyl, 3-chlorophenyl, 3,4-dichlorophenyl, 3,5-dichlorophenyl, 3-chloro-4-fluorophenyl, 3-methoxyphenyl, 4-methoxyphenyl, 3,4-dimethoxyphenyl, 4-methoxycarbonylphenyl, 4-carboxyphenyl, 4-(1,1-dimethylethyl)phenyl, 1-methylethyl and 4-methylphenyl.

11. The phenylimidazole compound according to claim 10, wherein, in General Formula (1), $R^4$ is a group selected from the group consisting of 2-thienyl, 3-thienyl, 3-furyl, phenyl, 4-fluorophenyl, 3-fluorophenyl, 3,4-difluorophenyl, 4-trifluoromethylphenyl, 3-trifluoromethylphenyl, 2-trifluoromethylphenyl, 4-chlorophenyl, 3-chlorophenyl, 3,4-dichlorophenyl, 3,5-dichlorophenyl, 3-chloro-4-fluorophenyl, 3-methoxyphenyl, 4-methoxycarbonylphenyl, 4-(1,1-dimethylethyl)phenyl, 1-methylethyl and 4-methylphenyl.

12. The phenylimidazole compound according to claim 1, wherein, in General Formula (1), $R^1$ is a pyridyl lower alkyl group optionally substituted with 1 or 2 substituents selected from the group consisting of halogen atoms, cyano group, and halogen-substituted lower alkyl groups.

13. The phenylimidazole compound according to claim 12, wherein, in General Formula (1), $R^1$ is a group selected from the group consisting of 5-trifluoromethyl-2-pyridylmethyl, 2-pyridylmethyl, 3-pyridylmethyl, 5-chloro-2-pyridylmethyl and 5-cyano-2-pyridylmethyl.

14. The phenylimidazole compound according to claim 1, wherein, in General Formula (1), $R^1$ is a pyridyl lower alkyl group optionally substituted with a halogen-substituted lower alkyl group.

15. The phenylimidazole compound according to claim 14, wherein, in General Formula (1), $R^1$ is a group selected from the group consisting of 2-pyridylmethyl and 6-trifluoromethyl-3-pyridylmethyl.

16. The phenylimidazole compound according to claim 1, wherein, in General Formula (1), $R^1$ is a group selected from the group consisting of benzyl, 4-chlorobenzyl and 4-bromo-2-fluorobenzyl, and $R^4$ is a group selected from the group consisting of 4-trifluoromethylphenyl, 4-fluorophenyl, 3,4-difluorophenyl, 4-chlorophenyl, 3,4-dichlorophenyl and 4-methylphenyl.

17. The phenylimidazole compound according to claim 1, selected from the following compounds:
4-[4-(4-bromo-2-fluorobenzyloxy)-3-methoxyphenyl]-2-[4-(trifluoromethyl)phenyl]-1H-imidazole
4-[4-(4-cyanobenzyloxy)-2-methoxyphenyl]-2-[4-(trifluoromethyl)phenyl]-1H-imidazole
4-[4-(4-bromo-2-fluorobenzyloxy)-2-methoxyphenyl]-2-[4-(trifluoromethyl)phenyl]-1H-imidazole
4-[4-(4-chlorobenzyloxy)-2-methoxyphenyl]-2-[4-(trifluoromethyl)phenyl]-1H-imidazole
4-(4-benzyloxy-3-methoxyphenyl)-2-(3-thienyl)-1H-imidazole
4-(4-benzyloxy-2-methoxyphenyl)-2-(4-fluorophenyl)-1H-imidazole
4-(4-benzyloxy-3-methoxyphenyl)-2-(4-fluorophenyl)-5-methyl-1H-imidazole 4-[4-(4-chlorobenzyloxy)-2-methoxyphenyl]-2-(4-fluorophenyl)-1H-imidazole
4-[4-(4-chlorobenzyloxy)-3-methoxyphenyl]-2-[4-(trifluoromethyl)phenyl]-1H-imidazole
4-[4-(4-cyanobenzyloxy)-2-methoxyphenyl]-2-(4-fluorophenyl)-1H-imidazole
4-[4-(4-bromo-2-fluorobenzyloxy)-3-methoxyphenyl]-2-(4-fluorophenyl)-1H-imidazole
4-[4-(4-bromo-2-fluorobenzyloxy)-2-methoxyphenyl]-2-(4-fluorophenyl)-1H-imidazole
4-[4-(4-bromo-2-fluorobenzyloxy)-2-methoxyphenyl]-2-(4-chlorophenyl)-1H-imidazole
4-[4-(4-bromo-2-fluorobenzyloxy)-3-methoxyphenyl]-2-(2-thienyl)-1H-imidazole
4-[4-(4-chlorobenzyloxy)-2-methoxyphenyl]-2-(3-thienyl)-1H-imidazole
4-[4-(4-cyanobenzyloxy)-2-methoxyphenyl]-2-[3-(trifluoromethyl)phenyl]-1H-imidazole
4-[4-(4-bromo-2-fluorobenzyloxy)-2-methoxyphenyl]-2-(4-methylphenyl)-1H-imidazole
4-[4-(4-chlorobenzyloxy)-2-methoxyphenyl]-2-(3,4-difluorophenyl)-1H-imidazole
4-(4-benzyloxy-2-methoxyphenyl)-2-(3,4-difluorophenyl)-1H-imidazole
4-(4-benzyloxy-2-methoxyphenyl)-2-(3,4-dichlorophenyl)-1H-imidazole.

18. The phenylimidazole compound according to claim 1, selected from the following compounds:
4-[4-(4-bromo-2-fluorobenzyloxy)-2-methoxyphenyl]-2-[4-(trifluoromethyl)phenyl]-1H-imidazole
4-[4-(4-chlorobenzyloxy)-2-methoxyphenyl]-2-[4-(trifluoromethyl)phenyl]-1H-imidazole
4-(4-benzyloxy-2-methoxyphenyl)-2-(4-fluorophenyl)-1H-imidazole
4-(4-benzyloxy-3-methoxyphenyl)-2-(4-fluorophenyl)-5-methyl-1H-imidazole
4-[4-(4-chlorobenzyloxy)-2-methoxyphenyl]-2-(4-fluorophenyl)-1H-imidazole
4-[4-(4-bromo-2-fluorobenzyloxy)-2-methoxyphenyl]-2-(4-fluorophenyl)-1H-imidazole
4-[4-(4-bromo-2-fluorobenzyloxy)-2-methoxyphenyl]-2-(4-chlorophenyl)-1H-imidazole
4-[4-(4-bromo-2-fluorobenzyloxy)-2-methoxyphenyl]-2-(4-methylphenyl)-1H-imidazole
4-[4-(4-chlorobenzyloxy)-2-methoxyphenyl]-2-(3,4-difluorophenyl)-1H-imidazole
4-(4-benzyloxy-2-methoxyphenyl)-2-(3,4-difluorophenyl)-1H-imidazole
4-(4-benzyloxy-2-methoxyphenyl)-2-(3,4-dichlorophenyl)-1H-imidazole
4-[4-(4-cyanobenzyloxy)-2-methoxyphenyl]-2-(4-fluorophenyl)-1H-imidazole.

19. A pharmaceutical composition containing, as an active ingredient, the compound according to claim 1.

20. An LPL activator containing, as an active ingredient, the compound according to claim 1.

21. An agent for preventing and treating hyperlipidemia containing, as an active ingredient, the compound according to claim 1.

22. An anti-arteriosclerotic agent containing, as an active ingredient, the compound according to claim 1.

23. An anti-obesity agent containing, as an active ingredient, the compound according to claim 1.

24. A method of activating LPL, for treating hyperlipidemia, arteriosclerosis, or obesity, comprising administering an effective amount of the compound according to claim 1 to a subject in need thereof.

* * * * *